(12) United States Patent
Ghinea

(10) Patent No.: US 10,927,179 B2
(45) Date of Patent: Feb. 23, 2021

(54) HUMAN FOLLICLE-STIMULATING HORMONE RECEPTOR (FSHR) EXTRACELLULAR DOMAIN ANTIBODIES AND METHODS OF USE THEREOF

(71) Applicants: INSERM—INSTITUT NATIONAL DE LA SANTE ET DE LA RECHERCHE MEDICALE, Paris (FR); INSTITUT CURIE, Paris (FR)

(72) Inventor: Nicolae Ghinea, Paris (FR)

(73) Assignees: INSERM—INSTITUT NATIONAL DE LA SANTÉ ET DE LA RECHERCHE MÉDICALE, Paris (FR); INSTITUT CURIE, Paris (FR)

( * ) Notice: Subject to any disclaimer, the term of this patent is extended or adjusted under 35 U.S.C. 154(b) by 0 days.

(21) Appl. No.: 16/494,891

(22) PCT Filed: Mar. 7, 2018

(86) PCT No.: PCT/EP2018/055613
§ 371 (c)(1),
(2) Date: Sep. 17, 2019

(87) PCT Pub. No.: WO2018/172078
PCT Pub. Date: Sep. 27, 2018

(65) Prior Publication Data
US 2020/0010556 A1   Jan. 9, 2020

(30) Foreign Application Priority Data
Mar. 20, 2017   (EP) .................................... 17305302

(51) Int. Cl.
C07K 16/28    (2006.01)
G01N 33/574   (2006.01)

(52) U.S. Cl.
CPC ... C07K 16/2869 (2013.01); G01N 33/57415 (2013.01); G01N 33/57434 (2013.01); *C07K 2317/565* (2013.01); *G01N 2333/726* (2013.01)

(58) Field of Classification Search
CPC .......... C07K 16/2869; C07K 2317/565; C07K 2317/92; G01N 33/57415; G01N 33/57434; G01N 2333/726; A61K 2039/505
See application file for complete search history.

(56) References Cited

U.S. PATENT DOCUMENTS 4,816,567 A   3/1989 Cabilly et al.

FOREIGN PATENT DOCUMENTS

WO    8304261 A1    12/1983
WO    2009103741 A2   8/2009

OTHER PUBLICATIONS

International Search Report for International Application No. PCT/EP2018/055613; International Filing Date: Mar. 7, 2018; dated Mar. 4, 2018; 4 pages.
Vannier, Brigitte, et al., "Anti-Human FSH Receptor Monoclonal Antibodies Immunochemical and Immunocytochemical Characterization of the Receptor", Biochemistry 1996, 35, pp. 1358-1366.
Written Opinion of the International Searching Authority for International Application No. PCT/EP2018/055613; International Filing Date: Mar. 7, 2018; dated Mar. 4, 2018; 6 pages.
Allahyari, Hossein, et al., "Immunotoxin: A new tool for cancer therapy", Tumor Biology, Feb. 2017; pp. 1-11.
Arap, Wadih, "Targeting the prostate for destruction through a vascular address", PNAS, Feb. 2002, vol. 99; No. 3; pp. 1527-1531.
Casscells, W., et al, "Isolation, characterization, and localization of heparin-binding growth factors in the heart", J. Clin Invest 1990 85(2) pp. 433-441.
Clackson, Tim et al., "Making antibody fragments using phage display libraries", Nature, Aug. 15, 1991, vol. 352; pp. 624-627.
Cote, Richard J. et al., "Generation of human monoclonal antibodies reactive with cellular antigens", Proc Natl. Acad Sci, Apr. 1983, vol. 80; pp. 2026-2030.
Edgar, Ben-Josef, et al. , "Hormone-Refractory Prostate Cancer Cells Express Functional Follicle-Stimulating Hormone Receptor (FSHR)", The Journal of Urology, 1999, vol. 161; pp. 970-976.
Eisenreich, Andreas, et al., "Tissue Factor: A Conventional or Alternative Target in Cancer Therapy", Clinical Chemistry, (2016); 62:4; pp. 563-570.
Figueroa, Jose A., et al., "Chimeric Antigen Receptor Engineering: A Right Step in the Evolution of Adoptive Cellular Immunotherapy", International Reviews of Immunology, (2015) 34, pp. 154-187.
Gromoll, Jorg, et al., "Characterization of the 5' flanking region of the human follicle-stimulating hormone receptor gene", Molecular and Cellular Endocrinology, (1994); 102; pp. 93-102.
Jain, Nareshkumar, et al., "Current ADC Linker Chemistry", Pharm Res (2015) 32; pp. 3526-3540.
Jain, Rakesh K., Normalizing Tumor Microenvironment to Treat Cancer: Bench to Bedside to Biomarkers, Journal of Clinical Oncology, Jun. 2013, vol. 31, No. 17; pp. 2205-2218.
Keereweer, Stijn, "Shifting Focus in Optical Image-Guided Cancer Therapy", Mol Imaging Biol (2013) 16; pp. 1-9.
Kohler, G., et al., "Continuous cultures of fused cells secreting antibody of predefined specificity", Nature, Aug. 1975; vol. 256; pp. 495-497.
Leuschner; Carola et al., Targeting Breast and Prostate Cancers Through Their Hormone Receptors, Biology of Reproduction, 73, (2005); pp. 860-865.
Mariani, Stefania, et al., "Expression and Cellular Localization of Follicle-Stimulating Hormone Receptor in Normal Human Prostate, Benign Prostatic Hyperplasia and Prostate Cancer"; Journal of Urology, Jun. 2006, vol. 175; pp. 2072-2077.

(Continued)

Primary Examiner — Robert S Landsman
(74) Attorney, Agent, or Firm — Cantor Colburn LLP

(57) ABSTRACT

The invention relates to anti-human follicle-stimulating hormone receptor antibodies. The invention also relates to use of the anti-human follicle-stimulating hormone receptor antibodies in the treatment of cancer. The present invention also relates to a process for detecting cancerous cells and a process for diagnosis cancer. The present invention finds an application in the therapeutic and diagnostic medical technical fields.

15 Claims, 6 Drawing Sheets

Specification includes a Sequence Listing.

(56) References Cited

OTHER PUBLICATIONS

Marks, James D. et al., "By-passing Immunization; Human Antibodies from V-gene Libraries Displayed on Phage", J. Mol. Biol., (1991) 222,; pp. 581-597.
Marusyk, Andriy, "Intra-tumour heterogeneity: a looking glass for cancer?", Nature Reviews, May 2012, vol. 12; pp. 323-334.
Neri, Dario et al., "Tumour Vascular Targeting", Nature, Jun. 2005, vol. 5; pp. 436-446.
Nolting, Birte, Chapter 5, "Linker Technologies for Antibody-Drug Conjugates", Laurent Ducry (ed.), Antibody-Drug Conjugates, Methods in Molecular Biology, (2013), vol. 1045; pp. 71-99.
Peterson, Vanessa M. et al., "Ascites analysis by a microfiuidic chip allows tumor-cell profiling", PNAS published online Dec. 2, 2013; pp. E4978-E4986.
Planeix, Francois, et al., "Endothelial follicle-stimulating hormone receptor expression in invasive breast cancer and vascular remodeling at tumor periphery", Journal of Experimental & Clinical Cancer Research (2015) 34; 12; pp. 1-9.
Radu, Aurelian, et al., "Expression of Follicle-Stimulating Hormone Receptor in Tumor Blood Vessels"; The New England Journal of Medicine; 2010; 363;17; pp. 1621-1630.
Renner, Marcus et al., "Follicle-stimulating hormonoe receptor expression in solf tissue sarcomas", Histopathology, 2013, 63, pp. 29-35.
Rezvani, Katayoun et al., "The Application of Natural Killer Cell Immunotherapy for the Treatment of Cancer", Frontiers in Immunology, Nov. 2015, vol. 6, 13 pages, Article 57B.
Roberts, W. Gregory et al.; "Neovasculature Induced by Vascular Endothelial Growth Factor Is Fenestrated", Cancer Research, Feb. 1997, 57; pp. 765-772.
Siemann, Dietmar W. et al., "Differentiation and Definition of Vascular-Targeted Therapies", Clinical Cancer Research, Jan. 15, 2005, vol. 11, pp. 416-420.
Siraj, Ahsan, et al., "Expression of follicle-stimulating hormone receptor by the vascular endothelium in tumor metastases", BMC Cancer, 2013, 13;246; 8 pages.
Tanaka, Eiichi, et al., "Real-Time Intraoperateive Assessment of the Extrahepatic Bile Ducts in Rats and Pigs Using Invisible Near-Infrared Fluorescent Light", Surgery, Jul. 2008; 144(1); pp. 39-48.
Thorpe, Philip E., "Vascular Targeting Agents as Cancer Therapeutics", Clinical Cancer Research, Jan. 2004, vol. 10, pp. 415-427.
Tsuchikama, Kyoji, et al., "Antibody-drug conjugates: recent advances in conjugation and linker chemistries", Protein Cell, 2018, 9(1) pp. 33-46.
Xu, Xiaoding, "Multifunctinal Envelope-Type siRNA Delivery Nanoparticle Platform for Prostate Cancer Therapy", ACS Nano.; Mar. 28, 2017, 11(3); pp. 2618-2627.
Yang, Wei-Ping, "CDR Walking Mutagenesis for the Affinity Maturation of a Potent Human Anti-HIV-1 Antibody into the Picomolar Range"; J. Mol Biol, (1995), 254; pp. 392-403.

```
SEQUENCE LISTING

<160> NUMBER OF SEQ ID NOS: 49

<210> SEQ ID NO 1
<211> LENGTH: 5
<212> TYPE: PRT
<213> ORGANISM: Artificial Sequence
<220> FEATURE:
<223> OTHER INFORMATION: Antibodies Heavy Chain CDR1

<400> SEQUENCE: 1

Gln Phe Tyr Val Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Antibodies Heavy Chain CDR1

<400> SEQUENCE: 2

Arg Gln Trp Val Ile
1               5

<210> SEQ ID NO 3
<211> LENGTH: 5
<212> TYPE: PRT
<213> ORGANISM: Artificial Sequence
<220> FEATURE:
<223> OTHER INFORMATION: Antibodies Heavy Chain CDR1

<400> SEQUENCE: 3

Lys Gln Trp Leu Leu
1               5

<210> SEQ ID NO 4
<211> LENGTH: 5
<212> TYPE: PRT
<213> ORGANISM: Artificial Sequence
<220> FEATURE:
<223> OTHER INFORMATION: Antibodies Heavy Chain CDR1

<400> SEQUENCE: 4

Arg Ser Trp Ile Leu
1               5

<210> SEQ ID NO 5
```

```
<211> LENGTH: 5
<212> TYPE: PRT
<213> ORGANISM: Artificial Sequence
<220> FEATURE:
<223> OTHER INFORMATION: Antibodies Heavy Chain CDR1

<400> SEQUENCE: 5

Lys Tyr Trp Thr Gln
1               5

<210> SEQ ID NO 6
<211> LENGTH: 17
<212> TYPE: PRT
<213> ORGANISM: Artificial Sequence
<220> FEATURE:
<223> OTHER INFORMATION: Antibodies Heavy Chain CDR2

<400> SEQUENCE: 6

Glu Ile Phe Pro Arg Thr Gly Asn Thr Asn Tyr Asn Glu Lys Phe Lys
1               5                   10                  15

Gly

<210> SEQ ID NO 7
<211> LENGTH: 17
<212> TYPE: PRT
<213> ORGANISM: Artificial Sequence
<220> FEATURE:
<223> OTHER INFORMATION: Antibodies Heavy Chain CDR2

<400> SEQUENCE: 7

Glu Ile Leu Pro Arg Asn Gly Asn Thr Asn Tyr Asn Glu Lys Phe Lys
1               5                   10                  15

Gly

<210> SEQ ID NO 8
<211> LENGTH: 17
<212> TYPE: PRT
<213> ORGANISM: Artificial Sequence
<220> FEATURE:
<223> OTHER INFORMATION: Antibodies Heavy Chain CDR2

<400> SEQUENCE: 8

Glu Ile Phe Pro Arg Asn Gly Asn Thr Asn Tyr Asn Glu Lys Phe Lys
1               5                   10                  15

Gly

<210> SEQ ID NO 9
<211> LENGTH: 17
<212> TYPE: PRT
<213> ORGANISM: Artificial Sequence
<220> FEATURE:
<223> OTHER INFORMATION: Antibodies Heavy Chain CDR2

<400> SEQUENCE: 9

Glu Ile Tyr Pro Gln Asn Gln Asn Thr Asn Tyr Asn Glu Lys Phe Lys
1               5                   10                  15

Gly

<210> SEQ ID NO 10
<211> LENGTH: 17
<212> TYPE: PRT
<213> ORGANISM: Artificial Sequence
<220> FEATURE:
<223> OTHER INFORMATION: Antibodies Heavy Chain CDR2
```

```
<400> SEQUENCE: 10

Glu Ile Tyr Pro Arg Asn Gly Asn Thr Asn Tyr Asn Glu Lys Phe Lys
1               5                   10                  15

Gly

<210> SEQ ID NO 11
<211> LENGTH: 17
<212> TYPE: PRT
<213> ORGANISM: Artificial Sequence
<220> FEATURE:
<223> OTHER INFORMATION: Antibodies Heavy Chain CDR2
<220> FEATURE:
<221> NAME/KEY: MISC_FEATURE
<222> LOCATION: (3)..(3)
<223> OTHER INFORMATION: Xaa can be F, L, or Y
<220> FEATURE:
<221> NAME/KEY: MISC_FEATURE
<222> LOCATION: (5)..(5)
<223> OTHER INFORMATION: Xaa can be R or Q
<220> FEATURE:
<221> NAME/KEY: MISC_FEATURE
<222> LOCATION: (6)..(6)
<223> OTHER INFORMATION: Xaa can be T or N
<220> FEATURE:
<221> NAME/KEY: MISC_FEATURE
<222> LOCATION: (7)..(7)
<223> OTHER INFORMATION: Xaa can be G or Q

<400> SEQUENCE: 11

Glu Ile Xaa Pro Xaa Xaa Xaa Asn Thr Asn Tyr Asn Glu Lys Phe Lys
1               5                   10                  15

Gly

<210> SEQ ID NO 12
<211> LENGTH: 11
<212> TYPE: PRT
<213> ORGANISM: Artificial Sequence
<220> FEATURE:
<223> OTHER INFORMATION: Antibodies Heavy Chain CDR3

<400> SEQUENCE: 12

Gly Pro Thr Ala Ser Gly Tyr Ala Met Asp Tyr
1               5                   10

<210> SEQ ID NO 13
<211> LENGTH: 16
<212> TYPE: PRT
<213> ORGANISM: Artificial Sequence
<220> FEATURE:
<223> OTHER INFORMATION: Antibodies light Chain CDR1

<400> SEQUENCE: 13

Arg Ser Ser Gln Ser Ile Val His Arg Asn Gly Asn Thr Tyr Leu Glu
1               5                   10                  15

<210> SEQ ID NO 14
<211> LENGTH: 7
<212> TYPE: PRT
<213> ORGANISM: Artificial Sequence
<220> FEATURE:
<223> OTHER INFORMATION: Antibodies Light Chain CDR2

<400> SEQUENCE: 14

Lys Val Ser Asn Arg Phe Ser
1               5

<210> SEQ ID NO 15
```

```
<211> LENGTH: 9
<212> TYPE: PRT
<213> ORGANISM: Artificial Sequence
<220> FEATURE:
<223> OTHER INFORMATION: Antibodies Light Chain CDR3

<400> SEQUENCE: 15

Phe Gln Gly Ser His Val Pro Phe Thr
1               5

<210> SEQ ID NO 16
<211> LENGTH: 5
<212> TYPE: PRT
<213> ORGANISM: Artificial Sequence
<220> FEATURE:
<223> OTHER INFORMATION: antibodie light chain CDR1
<220> FEATURE:
<221> NAME/KEY: MISC_FEATURE
<222> LOCATION: (1)..(1)
<223> OTHER INFORMATION: Xaa can be Q, R or K
<220> FEATURE:
<221> NAME/KEY: MISC_FEATURE
<222> LOCATION: (2)..(2)
<223> OTHER INFORMATION: Xaa can be F,Q,S or Y
<220> FEATURE:
<221> NAME/KEY: MISC_FEATURE
<222> LOCATION: (3)..(3)
<223> OTHER INFORMATION: Xaa can be Y or W
<220> FEATURE:
<221> NAME/KEY: MISC_FEATURE
<222> LOCATION: (4)..(4)
<223> OTHER INFORMATION: Xaa can be V, L, I or T
<220> FEATURE:
<221> NAME/KEY: MISC_FEATURE
<222> LOCATION: (5)..(5)
<223> OTHER INFORMATION: Xaa can be G, I, L or T

<400> SEQUENCE: 16

Xaa Xaa Xaa Xaa Xaa
1               5

<210> SEQ ID NO 17
<211> LENGTH: 120
<212> TYPE: PRT
<213> ORGANISM: Artificial Sequence
<220> FEATURE:
<223> OTHER INFORMATION: Antibody heavy chain

<400> SEQUENCE: 17

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Gln Phe
                20                  25                  30

Tyr Val Gly Trp Val Lys Gln Arg Pro Gly His Gly Leu Glu Trp Ile
            35                  40                  45

Gly Glu Ile Phe Pro Arg Thr Gly Asn Thr Asn Tyr Asn Glu Lys Phe
        50                  55                  60

Lys Gly Lys Ala Thr Phe Thr Ala Asp Thr Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Pro Thr Ala Ser Gly Tyr Ala Met Asp Tyr Trp Gly Gln
            100                 105                 110

Gly Thr Ser Val Thr Val Ser Ser
        115                 120
```

<210> SEQ ID NO 18
<211> LENGTH: 120
<212> TYPE: PRT
<213> ORGANISM: Artificial Sequence
<220> FEATURE:
<223> OTHER INFORMATION: antibody heavy chain

<400> SEQUENCE: 18

```
Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Arg Gln
                20                  25                  30

Trp Val Ile Trp Val Lys Gln Arg Pro Gly His Gly Leu Glu Trp Ile
            35                  40                  45

Gly Glu Ile Leu Pro Arg Asn Gly Asn Thr Asn Tyr Asn Glu Lys Phe
        50                  55                  60

Lys Gly Lys Ala Thr Phe Thr Ala Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Pro Thr Ala Ser Gly Tyr Ala Met Asp Tyr Trp Gly Gln
            100                 105                 110

Gly Thr Ser Val Thr Val Ser Ser
        115                 120
```

<210> SEQ ID NO 19
<211> LENGTH: 120
<212> TYPE: PRT
<213> ORGANISM: Artificial Sequence
<220> FEATURE:
<223> OTHER INFORMATION: antibodi heavy chain

<400> SEQUENCE: 19

```
Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Lys Gln
                20                  25                  30

Trp Leu Leu Trp Val Lys Gln Arg Pro Gly His Gly Leu Glu Trp Ile
            35                  40                  45

Gly Glu Ile Phe Pro Arg Asn Gly Asn Thr Asn Tyr Asn Glu Lys Phe
        50                  55                  60

Lys Gly Lys Ala Thr Phe Thr Ala Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Pro Thr Ala Ser Gly Tyr Ala Met Asp Tyr Trp Gly Gln
            100                 105                 110

Gly Thr Ser Val Thr Val Ser Ser
        115                 120
```

<210> SEQ ID NO 20
<211> LENGTH: 120
<212> TYPE: PRT
<213> ORGANISM: Artificial Sequence
<220> FEATURE:
<223> OTHER INFORMATION: antibody heavy chain

<400> SEQUENCE: 20

```
Gln Val Gln Leu Gln Gln Ser Gly Ala Glu Leu Met Lys Pro Gly Ala
1               5                   10                  15
```

```
Ser Val Lys Ile Ser Cys Lys Ala Thr Gly Tyr Thr Phe Ser Arg Ser
            20                  25                  30

Trp Ile Leu Trp Val Lys Gln Arg Pro Gly His Gly Leu Glu Trp Ile
        35                  40                  45

Gly Glu Ile Tyr Pro Gln Asn Gln Asn Thr Asn Tyr Asn Glu Lys Phe
    50                  55                  60

Lys Gly Lys Ala Thr Phe Thr Ala Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Pro Thr Ala Ser Gly Tyr Ala Met Asp Tyr Trp Gly Gln
            100                 105                 110

Gly Thr Ser Val Thr Val Ser Ser
            115                 120
```

<210> SEQ ID NO 21
<211> LENGTH: 120
<212> TYPE: PRT
<213> ORGANISM: Artificial Sequence
<220> FEATURE:
<223> OTHER INFORMATION: antibody heavy chain

<400> SEQUENCE: 21

```
Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Lys Tyr
            20                  25                  30

Trp Thr Gln Trp Val Lys Gln Arg Pro Gly His Gly Leu Glu Trp Ile
        35                  40                  45

Gly Glu Ile Tyr Pro Arg Asn Gly Asn Thr Asn Tyr Asn Glu Lys Phe
    50                  55                  60

Lys Gly Lys Ala Thr Phe Thr Ala Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Pro Thr Ala Ser Gly Tyr Ala Met Asp Tyr Trp Gly Gln
            100                 105                 110

Gly Thr Ser Val Thr Val Ser Ser
            115                 120
```

<210> SEQ ID NO 22
<211> LENGTH: 112
<212> TYPE: PRT
<213> ORGANISM: Artificial Sequence
<220> FEATURE:
<223> OTHER INFORMATION: antibody light chain

<400> SEQUENCE: 22

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Arg
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
```

```
                65                  70                  75                  80
            Ile Arg Val Glu Ala Glu Asp Leu Gly Val Tyr Tyr Cys Phe Gln Gly
                            85                  90                  95

Ser His Val Pro Phe Thr Phe Gly Ser Gly Thr Lys Leu Glu Ile Lys
                            100                 105                 110

<210> SEQ ID NO 23
<211> LENGTH: 336
<212> TYPE: DNA
<213> ORGANISM: Artificial Sequence
<220> FEATURE:
<223> OTHER INFORMATION: DNA coding antibody light chain

<400> SEQUENCE: 23
gatgtcttga tgacccaaac tccactctcc ctgcctgtca gtcttggaga tcaagcctcc      60
atctcttgca gatctagtca gagcattgta catagaaatg gaaacactta tttagaatgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
atcagagtgg aggctgagga tctgggagtt tattactgct ttcaaggttc acatgttcca     300
ttcacgttcg gctcggggac aaagttggaa ataaaa                               336

<210> SEQ ID NO 24
<211> LENGTH: 48
<212> TYPE: DNA
<213> ORGANISM: Artificial Sequence
<220> FEATURE:
<223> OTHER INFORMATION: nucleic acid coding the light chain CDR1

<400> SEQUENCE: 24
agatctagtc agagcattgt acatagaaat ggaaacactt atttagaa                   48

<210> SEQ ID NO 25
<211> LENGTH: 21
<212> TYPE: DNA
<213> ORGANISM: Artificial Sequence
<220> FEATURE:
<223> OTHER INFORMATION: nucleic acid coding the light chain CDR2

<400> SEQUENCE: 25
aaagtttcca accgattttc t                                                21

<210> SEQ ID NO 26
<211> LENGTH: 27
<212> TYPE: DNA
<213> ORGANISM: Artificial Sequence
<220> FEATURE:
<223> OTHER INFORMATION: nucleic acid coding the light chain CDR 3

<400> SEQUENCE: 26
tttcaaggtt cacatgttcc attcacg                                          27

<210> SEQ ID NO 27
<211> LENGTH: 112
<212> TYPE: PRT
<213> ORGANISM: Artificial Sequence
<220> FEATURE:
<223> OTHER INFORMATION: peptide Vk

<400> SEQUENCE: 27

Asp Val Leu Met Thr Gln Thr Pro Leu Ser Leu Pro Val Ser Leu Gly
1               5                   10                  15
```

Asp Gln Ala Ser Ile Ser Cys Arg Ser Ser Gln Ser Ile Val His Arg
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ile Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

<210> SEQ ID NO 28
<211> LENGTH: 360
<212> TYPE: DNA
<213> ORGANISM: Artificial Sequence
<220> FEATURE:
<223> OTHER INFORMATION: nucleic acid coding heavy chain comprising
      CDR1 - CDR 2 and CDR3

<400> SEQUENCE: 28
caggttcagc tgcagcagtc tggcgcggaa ctgatgaaac cgggcgcgag cgtgaaaatt      60
tcctgcaaag cgaccggcta ccttcagc cagttttatg tgggttgggt gaaacagcgc      120
ccgggtcatg gcctggaatg gattggcgaa attttttccta ggacgggtaa caccaactac     180
aacgaaaaat tcaaaggcaa agccaccttc accgcagata cctcctccag caccgcctac     240
atgcagctga gcagcctgac ctctgaagac tctgcggtgt attactgtgc aagaggcccg     300
accgcgagcg gctatgcgat ggactactgg ggtcagggca cctctgtgac cgtgtcctct     360

<210> SEQ ID NO 29
<211> LENGTH: 360
<212> TYPE: DNA
<213> ORGANISM: Artificial Sequence
<220> FEATURE:
<223> OTHER INFORMATION: nucleic acid coding heavy chain comprising
      CDR1 - CDR 2 and CDR3

<400> SEQUENCE: 29
caggttcagc tgcagcagtc tggcgcggaa ctgatgaaac cgggcgcgag cgtgaaaatt      60
tcctgcaaag cgaccggcta ccttcagc cggcagtggg ttatttgggt gaaacagcgc      120
ccgggtcatg gcctggaatg gattggcgaa attttgccga aaacggtaa caccaactac      180 aacgaaaaat tcaaaggcaa agccaccttc accgcagata cctcctccag caccgcctac     240
atgcagctga gcagcctgac ctctgaagac tctgcggtgt attactgtgc aagaggcccg     300
accgcgagcg gctatgcgat ggactactgg ggtcagggca cctctgtgac cgtgtcctct     360

<210> SEQ ID NO 30
<211> LENGTH: 360
<212> TYPE: DNA
<213> ORGANISM: Artificial Sequence
<220> FEATURE:
<223> OTHER INFORMATION: nucleic acid coding heavy chain comprising
      CDR1 - CDR 2 and CDR3

<400> SEQUENCE: 30
caggttcagc tgcagcagtc tggcgcggaa ctgatgaaac cgggcgcgag cgtgaaaatt      60
tcctgcaaag cgaccggcta ccttcagc aagcagtggt tgttgtgggt gaaacagcgc      120

```
ccgggtcatg gcctggaatg gattggcgaa attttccgc ggaacgggaa caccaactac    180
aacgaaaaat tcaaaggcaa agccaccttc accgcagata cctcctccag caccgcctac    240
atgcagctga gcagcctgac ctctgaagac tctgcggtgt attactgtgc aagaggcccg    300
accgcgagcg gctatgcgat ggactactgg ggtcagggca cctctgtgac cgtgtcctct    360
```

<210> SEQ ID NO 31
<211> LENGTH: 360
<212> TYPE: DNA
<213> ORGANISM: Artificial Sequence
<220> FEATURE:
<223> OTHER INFORMATION: nucleic acid coding heavy chain comprising
      CDR1 - CDR 2 and CDR3

<400> SEQUENCE: 31

```
caggttcagc tgcagcagtc tggcgcggaa ctgatgaaac cgggcgcgag cgtgaaaatt    60
tcctgcaaag cgaccggcta caccttcagc cgttcgtgga ttctgtgggt gaaacagcgc    120
ccgggtcatg gcctggaatg gattggcgaa atttatccgt agaactagaa caccaactac    180
aacgaaaaat tcaaaggcaa agccaccttc accgcagata cctcctccag caccgcctac    240
atgcagctga gcagcctgac ctctgaagac tctgcggtgt attactgtgc aagaggcccg    300
accgcgagcg gctatgcgat ggactactgg ggtcagggca cctctgtgac cgtgtcctct    360
```

<210> SEQ ID NO 32
<211> LENGTH: 360
<212> TYPE: DNA
<213> ORGANISM: Artificial Sequence
<220> FEATURE:
<223> OTHER INFORMATION: nucleic acid coding heavy chain comprising
      CDR1 - CDR 2 and CDR3

<400> SEQUENCE: 32

```
caggttcagc tgcagcagtc tggcgcggaa ctgatgaaac cgggcgcgag cgtgaaaatt    60
tcctgcaaag cgaccggcta caccttcagc aagtattgga ctcagtgggt gaaacagcgc    120
ccgggtcatg gcctggaatg gattggcgaa atttatccgc ggaacgggaa caccaactac    180
aacgaaaaat tcaaaggcaa agccaccttc accgcagata cctcctccag caccgcctac    240
atgcagctga gcagcctgac ctctgaagac tctgcggtgt attactgtgc aagaggcccg    300
accgcgagcg gctatgcgat ggactactgg ggtcagggca cctctgtgac cgtgtcctct    360
```

<210> SEQ ID NO 33
<211> LENGTH: 717
<212> TYPE: DNA
<213> ORGANISM: Artificial Sequence
<220> FEATURE:
<223> OTHER INFORMATION: light chain sequence

<400> SEQUENCE: 33

```
atgaagttgc ctgttaggct gttggtgctg atgttctgga ttcctgcttc agcagtgat     60 gtcttgatga cccaaactcc actctccctg cctgtcagtc ttggagatca agcctccatc    120
tcttgcagat ctagtcagag cattgtacat agaaatggaa acacttattt agaatggtac    180
ctgcagaaac caggccagtc tccaaagctc ctgatctaca agtttccaa ccgattttct    240 ggggtcccag acaggttcag tggcagtgga tcaggacag atttcacact caagatcatc    300
agagtggagg ctgaggatct gggagtttat tactgctttc aaggttcaca tgttccattc    360
acgttcggct cggggacaaa gttggaaata aaacgggctg atgctgcacc aactgtatcc    420
atcttcccac catccagtga gcagttaaca tctggaggtg cctcagtcgt gtgcttcttg    480
```

```
aacaacttct accccaaaga catcaatgtc aagtggaaga ttgatggcag tgaacgacaa      540
aatggcgtcc tgaacagttg gactgatcag gacagcaaag acagcaccta cagcatgagc      600
agcaccctca cgttgaccaa ggacgagtat gaacgacata cagctatac ctgtgaggcc       660 actcacaaga catcaacttc acccattgtc aagagcttca acaggaatga gtgttag        717
```

<210> SEQ ID NO 34
<211> LENGTH: 1407
<212> TYPE: DNA
<213> ORGANISM: Artificial Sequence
<220> FEATURE:
<223> OTHER INFORMATION: nucleic acid coding for amino acide sequence of
      the constant part of heavy chain

<400> SEQUENCE: 34

```
atgggctggt cctgcatcat cctgtttctg gtggccaccg ccacaggcgt ccactctcag      60
gtgcagctgc agcagtccgg cgccgaactg atgaagcctg cgcctccgt gaagatctcc      120 tgcaaggcca ccggatacac cttctcccag ttctacgtgg ctgggtgaa gcagaggcct      180 ggccacggac tggagtggat cggcgagatc ttccccagga ccggcaacac caactacaac     240
gagaagttca agggcaaggc caccttcacc gccgacacct cctccagcac cgcctacatg     300
cagctgtcct ccctgacctc cgaggactcc gccgtgtact actgcgctag ggccctaca     360 gcttccggct acgccatgga ctactgggga cagggcacct ccgtgaccgt gtcctccgct     420
aaaacaacag ccccatcggt ctatccactg gcccctgtgt gtggagatac aactggctcc     480
tcggtgactc taggatgcct ggtcaagggt tatttccctg agccagtgac cttgacctgg     540
aactctggat ccctgtccag tggtgtgcac accttccag ctgtcctgca gtctgacctc      600
tacaccctca gcagctcagt gactgtaacc tcgagcacct ggcccagcca gtccatcacc     660
tgcaatgtgg cccacccggc aagcagcacc aaggtggaca agaaaattga gcccagaggg     720
cccacaatca gccctgtcc tccatgcaaa tgcccagcac ctaacctctt gggtggacca      780
tccgtcttca tcttccctcc aaagatcaag gatgtactca tgatctccct gagccccata     840
gtcacatgtg tggtggtgga tgtgagcgag gatgacccag atgtccagat cagctggttt     900
gtgaacaacg tggaagtaca cacagctcag acacaaaccc atagagagga ttacaacagt     960
actctccggg tggtcagtgc cctccccatc cagcaccagg actggatgag tggcaaggag    1020
ttcaaatgca aggtcaacaa caaagacctc ccagcgccca tcgagagaac catctcaaaa    1080
cccaaagggt cagtaagagc tccacaggta tatgtcttgc ctccaccaga agaagagatg    1140
actaagaaac aggtcactct gacctgcatg gtcacagact tcatgcctga agacatttac    1200
gtggagtgga ccaacaacgg aaaacagag ctaaactaca agaacactga accagtcctg     1260
gactctgatg gttcttactt catgtacagc aagctgagag tggaaaagaa gaactgggtg    1320
gaaagaaata gctactcctg ttcagtggtc cacgagggtc tgcacaatca ccacgacgt    1380 aagagcttct cccggactcc gggtaaa                                        1407
```

<210> SEQ ID NO 35
<211> LENGTH: 1407
<212> TYPE: DNA
<213> ORGANISM: Artificial Sequence
<220> FEATURE:
<223> OTHER INFORMATION: nucleic acid coding for amino acide sequence of
      the constant part of heavy chain

<400> SEQUENCE: 35

```
atgggctggt cctgcatcat cctgtttctg gtggccaccg ccacaggcgt ccactctcag    60
gtgcagctgc agcagtccgg cgctgagctg atgaagcctg cgcctccgt gaagatctcc   120
tgcaaggcca ccggctacac cttctccagg cagtgggtga tctgggtgaa gcagaggcct   180
ggacacggcc tggagtggat cggcgagatc ctgccccgga acggcaacac caactacaac   240
gaaaagttca agggcaaggc caccttcacc gccgacacct cctcctccac cgcctacatg   300
cagctgtcct ccctgacctc cgaggactcc gccgtgtact actgtgctag ggcccctacc   360
gcctccggct atgccatgga ctactgggc agggcacat ccgtgaccgt gtcctccgct   420
aaaacaacag ccccatcggt ctatccactg gcccctgtgt gtggagatac aactggctcc   480
tcggtgactc taggatgcct ggtcaagggt tatttccctg agccagtgac cttgacctgg   540
aactctggat ccctgtccag tggtgtgcac accttcccag ctgtcctgca gtctgacctc   600
tacaccctca gcagctcagt gactgtaacc tcgagcacct ggcccagcca gtccatcacc   660
tgcaatgtgg cccacccggc aagcagcacc aaggtggaca gaaaattga gcccagaggg   720
cccacaatca gccctgtcc tccatgcaaa tgcccagcac ctaacctctt gggtggacca   780
tccgtcttca tcttccctcc aaagatcaag gatgtactca tgatctccct gagccccata   840
gtcacatgtg tggtggtgga tgtgagcgag gatgacccca atgtccagat cagctggttt   900
gtgaacaacg tggaagtaca cacagctcag acacaaaccc atagagagga ttacaacagt   960
actctccggg tggtcagtgc cctccccatc agcaccagg actggatgag tggcaaggag  1020
ttcaaatgca aggtcaacaa caaagacctc ccagcgccca tcgagagaac catctcaaaa  1080
cccaaagggt cagtaagagc tccacaggta tatgtcttgc ctccaccaga agaagagatg  1140
actaagaaac aggtcactct gacctgcatg gtcacagact tcatgcctga agacatttac  1200
gtggagtgga ccaacaacgg gaaaacagag ctaaactaca agaacactga accagtcctg  1260
gactctgatg gttcttactt catgtacagc aagctgagag tggaaaagaa gaactgggtg  1320
gaaagaaata gctactcctg ttcagtggtc cacgagggtc tgcacaatca ccacacgact  1380
aagagcttct cccggactcc gggtaaa                                      1407
```

<210> SEQ ID NO 36
<211> LENGTH: 1407
<212> TYPE: DNA
<213> ORGANISM: Artificial Sequence
<220> FEATURE:
<223> OTHER INFORMATION: nucleic acid coding for amino acid sequence of
      the constant part of heavy chain

<400> SEQUENCE: 36

```
atgggctggt cctgcatcat cctgtttctg gtggccaccg ccacaggcgt ccactctcag    60
gtgcagctgc agcagtccgg cgctgagctg atgaagcccg gagcctccgt gaagatcagc   120
tgcaaggcca ccggctacac cttctccaag cagtggctgc tgtgggtgaa gcagaggcct   180
ggccatggcc tggagtggat cggcgagatc ttccccggga acggcaacac caactacaac   240
gagaagttca agggcaaggc caccttcacc gccgacacct cctcctccac cgcctacatg   300
cagctgagct ccctgacctc cgaggactcc gccgtgtact actgtgctag ggacccaca   360
gcctccggct acgctatgga ctactggggc agggaacct ccgtgaccgt gtcctccgct   420
aaaacaacag ccccatcggt ctatccactg gcccctgtgt gtggagatac aactggctcc   480
tcggtgactc taggatgcct ggtcaagggt tatttccctg agccagtgac cttgacctgg   540
aactctggat ccctgtccag tggtgtgcac accttcccag ctgtcctgca gtctgacctc   600
```

```
tacaccctca gcagctcagt gactgtaacc tcgagcacct ggcccagcca gtccatcacc        660
tgcaatgtgg cccacccggc aagcagcacc aaggtggaca agaaaattga gcccagaggg        720
cccacaatca agccctgtcc tccatgcaaa tgcccagcac ctaacctctt gggtggacca        780
tccgtcttca tcttccctcc aaagatcaag gatgtactca tgatctccct gagccccata        840
gtcacatgtg tggtggtgga tgtgagcgag gatgacccag atgtccagat cagctggttt        900
gtgaacaacg tggaagtaca cacagctcag acacaaaccc atagagagga ttacaacagt        960
actctccggg tggtcagtgc cctccccatc cagcaccagg actggatgag tggcaaggag       1020
ttcaaatgca aggtcaacaa caaagacctc ccagcgccca tcgagagaac catctcaaaa       1080
cccaaagggt cagtaagagc tccacaggta tatgtcttgc ctccaccaga agaagagatg       1140
actaagaaac aggtcactct gacctgcatg gtcacagact tcatgcctga agacatttac       1200
gtggagtgga ccaacaacgg gaaaacagag ctaaactaca agaacactga accagtcctg       1260
gactctgatg gttcttactt catgtacagc aagctgagag tggaaaagaa gaactgggtg       1320
gaaagaaata gctactcctg ttcagtggtc acgagagggtc tgcacaatca ccacgact       1380 aagagcttct cccggactcc gggtaaa                                          1407
```

<210> SEQ ID NO 37
<211> LENGTH: 1407
<212> TYPE: DNA
<213> ORGANISM: Artificial Sequence
<220> FEATURE:
<223> OTHER INFORMATION: nucleic acid coding for amino acide sequence of
      the constant part of heavy chain

<400> SEQUENCE: 37

```
atgggctggt cctgcatcat cctgtttctg gtggccaccg ccacaggcgt ccactctcag         60
gtgcagctgc agcagtccgg agccgagctg atgaagcctg gcgcctccgt gaagatcagc        120
tgcaaggcca ccggctacac cttctccagg tcctggatcc gtgggtgaa gcagaggcct        180 ggccacggac tggagtggat cggcgagatc taccccagaa ccagaacac caactacaac        240 gagaagttca gggcaaggc cacccttcacc gccgacacct cctcctccac cgcctacatg        300
cagctgtcct ccctgaccctc cgaggacagc gccgtgtact actgcgctag ggccctacc        360 gcttccggct atgccatgga ctactggggc cagggcacat ccgtgaccgt gtcctccgct        420
aaaacaacag cccccatcgt ctatccactg gcccctgtgt gtggagatac aactggctcc        480
tcggtgactc taggatgcct ggtcaagggt tatttccctg agccagtgac cttgacctgg        540
aactctggat ccctgtccag tggtgtgcac accttcccag ctgtcctgca gtctgacctc        600
tacaccctca gcagctcagt gactgtaacc tcgagcacct ggcccagcca gtccatcacc        660
tgcaatgtgg cccacccggc aagcagcacc aaggtggaca agaaaattga gcccagaggg        720
cccacaatca agccctgtcc tccatgcaaa tgcccagcac ctaacctctt gggtggacca        780
tccgtcttca tcttccctcc aaagatcaag gatgtactca tgatctccct gagccccata        840
gtcacatgtg tggtggtgga tgtgagcgag gatgacccag atgtccagat cagctggttt        900
gtgaacaacg tggaagtaca cacagctcag acacaaaccc atagagagga ttacaacagt        960
actctccggg tggtcagtgc cctccccatc cagcaccagg actggatgag tggcaaggag       1020
ttcaaatgca aggtcaacaa caaagacctc ccagcgccca tcgagagaac catctcaaaa       1080
cccaaagggt cagtaagagc tccacaggta tatgtcttgc ctccaccaga agaagagatg       1140
actaagaaac aggtcactct gacctgcatg gtcacagact tcatgcctga agacatttac       1200
```

```
gtggagtgga ccaacaacgg gaaaacagag ctaaactaca agaacactga accagtcctg    1260
gactctgatg gttcttactt catgtacagc aagctgagag tggaaaagaa gaactgggtg    1320
gaaagaaata gctactcctg ttcagtggtc cacgagggtc tgcacaatca ccacacgact    1380
aagagcttct cccggactcc gggtaaa                                        1407

<210> SEQ ID NO 38
<211> LENGTH: 1407
<212> TYPE: DNA
<213> ORGANISM: Artificial Sequence
<220> FEATURE:
<223> OTHER INFORMATION: nucleic acid coding for amino acide sequence of
      the constant part of heavy chain

<400> SEQUENCE: 38
atgggctggt cctgcatcat cctgtttctg gtggccaccg ccacaggcgt ccactctcag      60
gtgcagctgc agcagtccgg cgctgagctg atgaagcccg cgcttccgt gaagatctcc     120 tgcaaggcca ccggctacac cttcagcaag tactggaccc agtgggtgaa gcagaggccc     180
ggacacggac tggagtggat cggcgagatc taccccagga acggcaacac caactacaac     240
gagaagttca gggcaaggc caccttcacc gccgacacat cctcctccac cgcctacatg     300
cagctgtcct ccctgaccct cgaggactcc gccgtgtact actgtgctag ggccctacc     360 gcctccggct atgccatgga ctactggggc cagggcacat ccgtgaccgt gtccagcgct     420
aaaacaacag ccccatcggt ctatccactg gcccctgtgt gtggagatac aactggctcc     480
tcggtgactc taggatgcct ggtcaagggt tatttccctg agccagtgac cttgacctgg     540
aactctggat ccctgtccag tggtgtgcac accttcccag ctgtcctgca gtctgacctc     600 tacacccctca gcagctcagt gactgtaacc tcgagcacct ggcccagcca gtccatcacc     660
tgcaatgtgg cccacccggc aagcagcacc aaggtggaca agaaaattga gcccagaggg     720
cccacaatca gccctgtcc tcatgcaaa tgcccagcac ctaacctctt gggtggacca     780
tccgtcttca tcttccctcc aaagatcaag gatgtactca tgatctccct gagccccata     840
gtcacatgtg tggtggtgga tgtgagcgag gatgacccag atgtccagat cagctggttt     900
gtgaacaacg tggaagtaca cacagctcag acacaaaccc atagagagga ttacaacagt     960
actctccggg tggtcagtgc cctccccatc cagcaccagg actggatgag tggcaaggag    1020
ttcaaatgca aggtcaacaa caaagacctc ccagcgccca tcgagagaac catctcaaaa    1080
cccaaagggt cagtaagagc tccacaggta tatgtcttgc ctccaccaga agaagagatg    1140
actaagaaac aggtcactct gacctgcatg gtcacagact tcatgcctga agacatttac    1200
gtggagtgga ccaacaacgg gaaaacagag ctaaactaca agaacactga accagtcctg    1260
gactctgatg gttcttactt catgtacagc aagctgagag tggaaaagaa gaactgggtg    1320
gaaagaaata gctactcctg ttcagtggtc cacgagggtc tgcacaatca ccacacgact    1380
aagagcttct cccggactcc gggtaaa                                        1407

<210> SEQ ID NO 39
<211> LENGTH: 15
<212> TYPE: DNA
<213> ORGANISM: Artificial Sequence
<220> FEATURE:
<223> OTHER INFORMATION: nucleic acid coding VH (CRD)1

<400> SEQUENCE: 39
cagttttatg tgggt                                                      15
```

```
<210> SEQ ID NO 40
<211> LENGTH: 15
<212> TYPE: DNA
<213> ORGANISM: Artificial Sequence
<220> FEATURE:
<223> OTHER INFORMATION: nucleic acid coding VH CDR1

<400> SEQUENCE: 40
cggcagtggg ttatt                                                    15

<210> SEQ ID NO 41
<211> LENGTH: 15
<212> TYPE: DNA
<213> ORGANISM: Artificial Sequence
<220> FEATURE:
<223> OTHER INFORMATION: nucleic acid coding for VH CDR1

<400> SEQUENCE: 41
aagcagtggt tgttg                                                    15

<210> SEQ ID NO 42
<211> LENGTH: 15
<212> TYPE: DNA
<213> ORGANISM: Artificial Sequence
<220> FEATURE:
<223> OTHER INFORMATION: nucleic acid VH CDR1

<400> SEQUENCE: 42
aagcagtggt tgttg                                                    15

<210> SEQ ID NO 43
<211> LENGTH: 15
<212> TYPE: DNA
<213> ORGANISM: Artificial Sequence
<220> FEATURE:
<223> OTHER INFORMATION: nucleic acid coding VH CDR1

<400> SEQUENCE: 43
aagcagtggt tgttg                                                    15

<210> SEQ ID NO 44
<211> LENGTH: 50
<212> TYPE: DNA
<213> ORGANISM: Artificial Sequence
<220> FEATURE:
<223> OTHER INFORMATION: nucleic acid coding for VH CDR2

<400> SEQUENCE: 44 gaaattttc ctaggacggg taacaccaac tacaacgaaa aattcaaagg               50

<210> SEQ ID NO 45
<211> LENGTH: 50
<212> TYPE: DNA
<213> ORGANISM: Artificial Sequence
<220> FEATURE:
<223> OTHER INFORMATION: nucleic acid coding for VH CDR2

<400> SEQUENCE: 45 gaaatttgc cgagaaacgg taacaccaac tacaacgaaa aattcaaagg                50

<210> SEQ ID NO 46
<211> LENGTH: 51
<212> TYPE: DNA
<213> ORGANISM: Artificial Sequence
<220> FEATURE:
<223> OTHER INFORMATION: nucleic acid coding for VH CDR2
```

```
<400> SEQUENCE: 46 gaaattttc cgcggaacgg gaacaccaac tacaacgaaa aattcaaagg c        51

<210> SEQ ID NO 47
<211> LENGTH: 51
<212> TYPE: DNA
<213> ORGANISM: Artificial Sequence
<220> FEATURE:
<223> OTHER INFORMATION: nucleic acid coding VH CDR2

<400> SEQUENCE: 47
gaaatttatc cgtagaacta gaacaccaac tacaacgaaa aattcaaagg c        51

<210> SEQ ID NO 48
<211> LENGTH: 51
<212> TYPE: DNA
<213> ORGANISM: Artificial Sequence
<220> FEATURE:
<223> OTHER INFORMATION: nucleic acid coding VH CDR2

<400> SEQUENCE: 48
cgaaatttat ccgcggaacg ggaacaccaa ctacaacgaa aaattcaaag g        51

<210> SEQ ID NO 49
<211> LENGTH: 33
<212> TYPE: DNA
<213> ORGANISM: Artificial Sequence
<220> FEATURE:
<223> OTHER INFORMATION: nucleic acid coding VH CDR3

<400> SEQUENCE: 49
ggcccgaccg cgagcggcta tgcgatggac tac                            33
```

HUMAN FOLLICLE-STIMULATING HORMONE RECEPTOR (FSHR) EXTRACELLULAR DOMAIN ANTIBODIES AND METHODS OF USE THEREOF

CROSS REFERENCE TO RELATED APPLICATIONS

This application is a National Stage application of PCT/EP2018/055613, filed on Mar. 7, 2018, which claims the benefit of EP Application No. 17305302.6, filed on Mar. 20, 2017, both of which are incorporated by reference in their entirety herein.

FIELD OF THE INVENTION

The invention relates to anti-human follicle-stimulating hormone receptor antibodies. The invention also relates to use of the anti-human follicle-stimulating hormone receptor antibodies in the treatment of cancer.

The present invention also relates to a process for detecting cancerous cells and a process for cancer diagnosis.

The present invention finds application in the therapeutic and diagnostic medical technical fields.

In the description below, the references between square brackets ([ ]) refer to the list of references given at the end of the text.

BACKGROUND OF THE INVENTION

Cancer remains the most common malignancy and second-most common cause of death in the Western world. Early detection is essential for curative cancer therapy and for achieving a decrease in cancer mortality.

Improved molecular understanding of cancers has resulted in identification of various cancer cell targets for use in diagnostic and therapeutic interventions. However, tumor heterogeneity (phenotypic and genetic) is the first problem that currently challenges tumor-specific diagnosis, imaging and therapy [Marusyk et al., 2012 [1]; Keereweer et al., 2014 [2]].

The problem of tumor heterogeneity can be reduced by targeting the tumor-associated vasculature. The latter, a ubiquitous component of cancer, is essential for tumor growth and metastasis [Folkman 1990[3]]. Inhibition of angiogenesis (formation of new tumor blood vessels) and selective occlusion of tumor core vessels (vascular targeting) are considered as two of the practical approaches that may block tumor growth [Siemann et al 2005 [4]; Thorpe 2004[5]]. However, deleterious tumor processes (i.e. increased interstitial fluid pressure, protease secretion, acidosis, and focal necrosis) affect the tumor core vascular morphology, resulting in a grossly defective pathological vasculature [Roberts and Palade 1997 [6]]. Vascular normalization and/or decompression of tumor core vessels are required to improve delivery and efficacy of cytotoxic therapies [Jain 2013 [7]].

The efficacy of current antivascular therapies is also substantially compromised by the inability of drugs to kill tumor cells (TCs) located at the periphery of the tumor mass [Neri and Bicknell 2005 [8]] at which point TCs obtain oxygen and nutrients from unaffected peritumoral blood vessels.

All these therapies have to be improved since they do not allow to effectively treat all the different cancers and have varying efficiencies due to the high diversity of cancer.

There is therefore a real need to find a method and/or a compound which allows more efficient treatment and/or effective treatment of more varied cancers. In particular there is a real need to find new strategies, i.e. new targets/pathways, in the treatment of cancer.

The presence of specific endothelial cell proteins exposed on the luminal surface of peritumoral vessels should offer an opportunity for marker-specific delivery of drugs. For example, FSHR is expressed in all tumor types analyzed, for all tumor grades and stages examined [Radu et al 2010 [9]]. FSHR is present in the tumor endothelial cells (ECs), at the periphery of the tumors [Radu et al 2010 [9]; Renner et al 2013 [10]; Siraj et al 2013 [11]; Planeix et al 2015 [12]], and is absent in the normal tissues. A mouse tumor model showed that FSHR is present on the luminal surface of ECs in tumors and that it can specifically internalize ligands delivered in the circulation [Radu et al 2010 [9]]. Since FSHR is a common marker of peritumoral vessels, a single therapeutic agent should in principle be applicable to a wide range of tumor types.

Follicle-stimulating hormone receptor (FSHR) is a GTP-binding protein (G protein)-coupled receptor. In healthy humans, FSHR is expressed as a membrane glycoprotein only in target cells (Sertoli cells in testis and granulosa cells in the ovary). FSHR has a large glycosylated extracellular domain which represents approximately half of the receptor. This extracellular domain is involved in hormone binding and is encoded by the first nine exons of FSHR gene. Last exon, exon 10, encodes both the transmembrane and the intracellular domains [Gromoll et al., 1994 [13]].

In view of these findings, a number of murine, rabbit and goat monoclonal antibodies against FSHR have been developed and tested for their ability to detect tumor cells in vitro and in vivo. Although some antibodies raised against the human FSHR are available on the market, most of them are of low specificity [Peterson et al., 2013 [14]]. The specific FSHR323 monoclonal antibody recognizes the extracellular domain of FSHR [Vannier et al 1996 [15]]. However, the known compounds, for example antibodies have low specificity and do not provide reproducible and reliable detection of tumors cells in vivo. In particular, it is clearly known that only very high affinity anti-receptor antibodies could succeed in cancer imaging, diagnosis, and therapy [Yang et al 1995 [16]. Thus, since the above mentioned compounds have low specificity, they are not effective and cannot be used in any treatment of disease involving cancerous cells. Thus, there is clearly a need to find compounds which allow site-specific delivery of therapeutic and imaging agents. Indeed, this is an ongoing ultimate goal of the pharmaceutical industry in order to maximize agent action and minimize side effects.

In summary, new methods and/or compounds are needed which allow more efficient treatment of cancer and/or effective treatment of more varied cancers. In particular there is a real need to find new strategies, such as new targets and pathways, in the treatment of cancer. In addition, there is a need to find methods and/or compounds that can effectively and in a reliable manner detect cancerous cells.

DESCRIPTION OF THE INVENTION

The present invention meets these needs and overcomes the abovementioned drawbacks of the prior art by providing antibodies directed against the human follicle-stimulating hormone receptor (FSHR).

In particular, the antibodies of the present invention have a very high affinity (in the sub-nM range) anti-human FSHR.

In particular, the inventor has demonstrated that the antibodies of the present invention have a higher affinity and specificity than the known antibodies, in particular the results obtained (EC 50) with the antibodies of the present invention were from 7.5 to 18.2-fold higher than that of a known antibody. In addition, for immunohistochemical techniques with paraffin embedded tissues, the optimal concentration of the antibodies of the present invention, for example, was 5 to 25 fold less than a known antibody against human FSHR.

Moreover, the inventor has demonstrated that when used in immunolabeling techniques, for example immunofluorescence and/or as imaging agent, for example marked antibodies, the antibodies of the present invention allow to detect/to label FSHR when used at concentration, for example 33-fold lower than the optimal concentration of the known/commercially available antibodies. In other words, the antibodies of the present invention can be used at concentration at least 30 fold lower than the known antibodies and allow to obtain at least the same results. In addition, the antibodies of the present invention can effectively and in a reliable manner detect/label cancerous cells without using a high concentration of antibodies. In addition, when used at higher concentration, the antibodies of the present invention may label/detect FSHR which may not be detected by the known/commercially available antibodies.

The present invention provides an isolated antibody directed against the human follicle-stimulating hormone receptor (FSHR), or antigen-binding portion thereof, comprising at least one of the group comprising:
  A variable heavy (VH) chain complementarity-determining region (CDR)1 having the amino acid sequence XaXbXcXdXe (SEQ ID NO 16) wherein Xa is Q, R or K; Xb is F, Q, S or Y, Xc is Y or W, Xd is V, L, I or T, and Xe is G, I, L, Q or T,
  A variable heavy (VH) chain complementarity-determining region (CDR) 2 having the amino acid sequence EIXfPXgXhXiNTNYNEKFKG (SEQ ID NO 11) wherein Xf is F, L or Y, Xg is R or Q, Xh T or N and Xi G or Q,
  A variable heavy (VH) chain complementarity-determining region (CDR) 3 having the amino acid sequence GPTASGYAMDY (SEQ ID NO 12).

In the present "CDR" means the three hypervariable regions of the variable regions of the heavy and light chains of an antibody which constitute the elements of the paratope and make it possible to determine the complementarity of the antibody with the antigen's epitope. These three hypervariable regions are framed by four constant regions which constitute the "framework" (FR or framework regions) and give a stable configuration to the variable domain. Since, the amino acid sequences of the CDRs determine the shape and ionic properties of the antigen-binding site, the CDRs define the specificity of the antibody.

In the present "antibody" means monoclonal antibodies (including full length monoclonal antibodies), multispecific antibodies (e.g. bispecific antibodies), and antibody fragments so long as they exhibit the desired biological activity or function.

In the present "antibody fragments" or "antigen-binding portion" means a portion of a full length antibody, for example the antigen binding or variable region thereof. Examples of antibody fragments include Fab, Fab', F(ab')2, and scFv fragments. In the present "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are pure antibodies with single antigenic determinant specificities.

In the present, the "antibody antigen-binding portion thereof" may comprise at least a portion of one heavy- or one light-chain variable region domain comprising the three CDRs. It may be for example the scFv fragment which comprises a dimer of one heavy- and one light-chain variable region domain in tight, non-covalent association.

The present invention also provides an isolated antibody directed against the human follicle-stimulating hormone receptor (FSHR), or antigen-binding portion thereof as defined above further comprising at least one of the group comprising
  A variable light chain (VL) complementarity determining region (CDR)1 having the amino acid sequence RSSQSIVHRNGNTYLE (SEQ ID NO 13),
  A variable light chain (VL) complementarity determining region (CDR)2 having the amino acid sequence KVSNRFS (SEQ ID NO 14) and
  A variable light chain (VL) complementarity determining region (CDR)3 having the amino acid sequence FQGSHVPFT (SEQ ID NO 15).

In other words, the present invention also relates to an isolated antibody directed against the human follicle-stimulating hormone receptor (FSHR), or antigen-binding portion thereof, comprising at least one of the group comprising:
  A variable heavy (VH) chain complementarity determining region (CDR)1 having the amino acid sequence XaXbXcXdXe (SEQ ID NO 16) wherein Xa is Q, R or K; Xb is F, Q, S or Y, Xc is Y or W, Xd is V, L, I or T, and Xe is G, I, L, Q or T,
  A variable heavy (VH) chain complementarity determining region (CDR) 2 having the amino acid sequence EIXfPXgXhXiNTNYNEKFKG (SEQ ID NO 11) wherein Xf is F, L or Y, Xg is R or Q, Xh T or N and Xi G or Q,
  A variable heavy (VH) chain complementarity determining region (CDR) 3 having the amino acid sequence GPTASGYAMDY (SEQ ID NO 12), and
at least one of the group comprising:
  A variable light chain (VL) complementarity determining region (CDR)1 having the amino acid sequence RSSQSIVHRNGNTYLE (SEQ ID NO 13),
  A variable light chain (VL) complementarity determining region (CDR)2 having the amino acid sequence KVSNRFS (SEQ ID NO 14) and
  A variable light chain (VL) complementarity determining region (CDR)3 having the amino acid sequence FQGSHVPFT (SEQ ID NO 15).

In the present invention the variable heavy (VH) chain complementarity determining region (CDR)1 amino acid sequence of the isolated antibody directed against the human follicle-stimulating hormone receptor (FSHR), or antigen-binding portion thereof may be selected from the group comprising QFYVG (SEQ ID NO 1), RQWVI (SEQ ID NO 2), KQWLL (SEQ ID NO 3), RSWIL (SEQ ID NO 4) and KYWTQ (SEQ ID NO 5).

In the present invention the variable heavy (VH) chain complementarity determining region (CDR)2 amino acid sequence of the isolated antibody directed against the human follicle-stimulating hormone receptor (FSHR), or antigen-binding portion thereof may be selected from the group comprising EIFPRTGNTNYNEKFKG (SEQ ID NO 6), EILPRNGNTNYNEKFKG (SEQ ID NO 7), EIFPRNGNTNYNEKFKG (SEQ ID NO 8), EIYPQNQNTNYNEKFKG (SEQ ID NO 9), and EIY-PRNGNTNYNEKFKG (SEQ ID NO 10).

In the present invention the isolated antibody directed against the human follicle-stimulating hormone receptor (FSHR), or antigen-binding portion thereof may comprise the variable heavy (VH) chain complementarity determining region (CDR)1 and variable heavy (VH) chain complementarity determining region (CDR)2 amino acid sequence as defined in table 1 below

TABLE 1 variable heavy (VH) chain complementarity determining region (CDR)1 and variable heavy (VH) chain complementarity determining region (CDR)2 amino acid sequence

| VH CDR1 | VH CDR2 |
|---|---|
| QFYVG (SEQ ID NO 1) | EIFPRTGNTNYNEKFKG (SEQ ID NO 6) |
| RQWVI (SEQ ID NO 2) | EILPRNGNTNYNEKFKG (SEQ ID NO 7) |
| KQWLL (SEQ ID NO 3) | EIFPRNGNTNYNEKFKG (SEQ ID NO 8) |
| RSWIL (SEQ ID NO 4) | EIYPQNQNTNYNEKFKG (SEQ ID NO 9) |
| KYWTQ (SEQ ID NO 5) | EIYPRNGNTNYNEKFKG (SEQ ID NO 10) |

In the present invention, the sequence of the heavy chain of the isolated antibody directed against the human follicle-stimulating hormone receptor (FSHR), or antigen-binding portion thereof may comprise a peptide selected from the group comprising QVQLQQSGAELMKPGASVKISCK-ATGYTFSQFYVGWVKQRPGHGLEWI GEIF-PRTGNTNYNEKFKGKATFTADTSSSTAYMQLSSLT-SEDSAVYYCAR GPTASGYAMDYWGQGTSVTVSS (SEQ ID NO 17), QVQLQQSGAELMKPGASVKISCK-ATGYTFSRQWVIWVKQRPGHGLEWI GEILPRNG-NTNYNEKFKGKATFTADTSSSTAYMQLSSLTSED-SAVYYCAR GPTASGYAMDYWGQGTSVTVSS (SEQ ID NO 18), QVQLQQSGAELMKPGASVKISCK-ATGYTFSKQWLLWVKQRPGHGLEWI GEIFPRNG-NTNYNEKFKGKATFTADTSSSTAYMQLSSLTSED-SAVYYCA RGPTASGYAMDYWGQGTSVTVSS (SEQ ID NO 19), QVQLQQSGAELMKPGASVKISCK-ATGYTFSRSWILWVKQRPGHGLEWI GEI-YPQNQNTNYNEKFKGKATFTADTSSSTAYMQLSSLT-SEDSAVYYCA RGPTASGYAMDYWGQGTSVTVSS (SEQ ID NO 20) and QVQLQQSGAELMKPGASVKIS-CKATGYTFSKYWTQWVKQRPGHGLEWI GEIY-PRNGNTNYNEKFKGKATFTADTSSSTAYMQLSSLT-SEDSAVYYCA RGPTASGYAMDYWGQGTSVTVSS (SEQ ID NO 21).

In the present invention, the sequence of the light chain of the isolated antibody directed against the human follicle-stimulating hormone receptor (FSHR), or antigen-binding portion thereof may comprise a peptide of sequence DVLMTQTPLSLPVSLGDQASISCRSSQSIVH RNGN-TYLEWYLQKPGQSP KLLIYKVSNRFSGVPDRFSGSGSGTDFTLKIIRVEAE-DLGVYYCFQGSHV PFTFGSGTKLEIK (SEQ ID NO 22)

The antibodies of the present invention have a very high affinity anti-human FSHR specificity and more than the known antibodies. The isolated antibody(ies) directed against the human follicle-stimulating hormone receptor (FSHR), or antigen-binding portion thereof of the invention should provide a better cancer treatment efficiency. For example the isolated antibody directed against the human follicle-stimulating hormone receptor (FSHR), or antigen-binding portion thereof blocks FSH induced activation of adenylate cyclase, a FSH/FSHR signaling pathway involved in cancer cell proliferation [Ben-Josef et al 1999 [17]; Mariani et al 2006 [18]].

In the present "tumor" refers to an abnormal growth of tissue resulting from an abnormal multiplication of cells. A tumor may be benign, premalignant, or malignant (i.e. cancerous). A tumor may be a primary tumor, or a metastatic lesion.

In the present cancer may be any cancer known to one skilled in the art. It may be for example any disease involving abnormal cell growth with the potential to invade or spread to other parts of the body. It may be for example cancer of any organ or tissue of a human or of an animal. It may be for example a cancer selected from the group comprising lung, liver, eye, heart, lung, breast, bone, bone marrow, brain, head & neck, esophageal, tracheal, stomach, colon, pancreatic, cervical, uterine, bladder, prostate, testicular, skin, rectal, and lymphomas.

Another object of the present invention is a pharmaceutical composition comprising the antibody or antigen-binding portion thereof and a pharmaceutically acceptable carrier.

The antibody or antigen-binding portion thereof is as defined above.

The pharmaceutical composition may be in any form that can be administered to a human or an animal. The person skilled in the art clearly understands that the term "form" as used herein refers to the pharmaceutical formulation of the medicament for its practical use. For example, the medicament may be in a form selected from the group comprising an injectable form, an oral suspension, a pellet, a powder, granules or topical form (e.g. cream, lotion, collyrium).

The pharmaceutically acceptable carrier may be any known pharmaceutical support used for the administration of an antibody, or antigen-binding portion thereof, to a human or animal, depending on the subject to be treated. The pharmaceutical form or method of administering a pharmaceutical composition may be selected with regard to the human or animal subject to be treated. For example, for a child, for example from 1 to 17 years old, or a baby, for example under 1 year old, a syrup or an injection is preferred. Administration may for example be carried out with a weight graduated pipette, a syringe. For example, for an adult over 17 years old, an injection may be preferred. Administration may be carried out with an intravenous weight graduated syringe.

According to the present invention, the pharmaceutical composition may comprise any pharmaceutically acceptable and effective amount of antibody or antigen-binding portion thereof.

For example, in the case of cancer, the therapeutically effective amount of the antibody or antigen-binding portion thereof may reduce the number of cancer cells; reduce the tumor size; inhibit (i.e. slow to some extent and preferably stop) cancer cell infiltration into peripheral organs; inhibit (i.e. slow to some extent and preferably stop) tumor metastasis;

inhibit, to some extent, tumor growth; and/or relieve to some extent one or more of the symptoms associated with the cancer.

For example, the therapeutically effective amount of the antibody or antigen-binding portion thereof may be for example a daily dose of less than or equal to 5 mg/kg of body weight of the patient.

For example, pharmaceutical composition may comprise a concentration of antibody or antigen-binding portion thereof from 10 to 40 mg·ml$^{-1}$ of the pharmaceutical composition, for example from 15 to 30 mg·ml$^{-1}$ of the pharmaceutical composition, for example from 20 to 27.5 mg·ml$^{-1}$ of the pharmaceutical composition.

As previously mentioned, the inventor has also surprisingly demonstrated and is the first to demonstrate that isolated antibodies directed against the human follicle-stimulating hormone receptor (FSHR), or antigen-binding portion thereof of the invention allow treatment of disease, for example those in which the FSHR is involved, for example cancer, for example breast cancer. For example the isolated antibody directed against the human follicle-stimulating hormone receptor (FSHR), or antigen-binding portion thereof can block FSH induced activation of adenylate cyclase, a FSH/FSHR signaling pathway involved in cancer cell proliferation [Ben-Josef et al 1999 [17]; Mariani et al 2006 [18]].

Accordingly another object of the present invention is an antibody against the human follicle-stimulating hormone receptor (FSHR) or antigen-binding portion thereof for use as medicament. The antibody against the human follicle-stimulating hormone receptor (FSHR) or antigen-binding portion thereof is as defined above.

According to the present invention, the medicament may be a medicament for treating disease in which the FSHR receptor may be involved. For example, the medicament of the present invention may be a medicament for treating benign or malignant disease in which the FSHR is involved, it may be for example a disease selected from the group comprising endometriosis, leiomyoma, colon adenoma, benign prostatic hyperplasia, cancer, for example solid tumors, and sarcomas.

The medicament may be in any form that can be administered to a human or an animal. It may for example be a pharmaceutical composition as defined above.

The administration of the medicament may be carried out by any way known to one skilled in the art. It may, for example, be carried out directly, i.e. pure or substantially pure, or after mixing of the antibody or antigen-binding portion thereof with a pharmaceutically acceptable carrier and/or medium. According to the present invention, the medicament may be an injectable solution, a medicament for oral administration, for example selected from the group comprising a liquid formulation, a multiparticle system, an orodispersible dosage form. According to the present invention, the medicament may be a medicament for oral administration selected from the group comprising a liquid formulation, an oral effervescent dosage form, an oral powder, a multiparticle system, an orodispersible dosage form.

The antibody against the human follicle-stimulating hormone receptor (FSHR) or antigen-binding portion thereof may also be associated directly or with a linker to compound useful in the treatment of cancer.

In the present the compound useful in the treatment of cancer may be any compound known to one skilled in the art capable of being adapted to be bound directly or with a linker to an antibody or antigen-binding portion thereof. These may for example be radioisotopes, such as those disclosed in Peter J Hoskin, Radiotherapy in Practice— Radioisotope Therapy, 2007 [19], small molecules blocking the cell microtubules, such as 6-mercaptopurine, siRNAs, for example siRNA delivery system to silence PHB1 expression in prostate cancer (Xu X et al 2017 [20]), toxins, for example saporin, gelonin, ricin, shiga toxin, etc. (for review see Allahyari H et al 2017 [21]), tissue factors, for example membrane-bound full-length tissue factor or soluble alternatively spliced tissue factor (Eisenreich A et al. [22]), peptides, for example $_D$(KLAKLAK)$_2$ disclosed in Arap et al [23]; Leuschner and Hansel 2005 [24].

In the present the linker may be any linker known to one skilled in the art adapted for use with the present invention. It may be for example a linker disclosed in Nolting 2013 [25]; Jain et al 2015 [26]; Tsuchikama and An 2015 [27].

The inventor's work demonstrating the selective expression pattern of FSHR on the surface of tumor vessels [Radu et al 2010 [9]; Siraj et al 2013 [13]; Renner et al 2013 [10]; Planeix et al 2015 [12]] highlights the therapeutic potential of targeting FSHR for cancer therapies. The antibody against the human follicle-stimulating hormone receptor (FSHR) or antigen-binding portion thereof of the invention may be used as a component of a cell or a component of a cell (ex., T cells, NK cells) based immunotherapy using a chimeric antigen receptor (CAR) (Rezvani and Rouce 2015 [28]; Figueroa et al 2015 [29]).

Advantageously when the antibody against the human follicle-stimulating hormone receptor (FSHR) or antigen-binding portion thereof of the invention is used as a component of a cell or a component of a cell, for example T cells or NK cells, based immunotherapy using a chimeric antigen receptor (CAR), these cells targets the vascular endothelial FSHR expressed in peripheral tumor blood vessels. In addition and advantageously, the antibody against the human follicle-stimulating hormone receptor (FSHR) or antigen-binding portion thereof of the invention allows directing T cells to recognize and attack the tumor vasculature through the expression of chimeric antigen receptors (CARs) comprising the scFv fragment of the present antibodies specific for the FSHR antigen linked to T cell receptor signaling domains and may be used as a medicament for the treatment of cancer, for example as an immunotherapeutic strategy for the treatment of tumors in cancer patients.

The inventor has also surprisingly demonstrated for the first time that isolated antibodies directed against the human follicle-stimulating hormone receptor (FSHR), or antigen-binding portion thereof of the invention target FSHR, in particular expressed at the surface of cancerous cells, and allow to detect/target cells expressing the FSHR. In addition cells expressing FSHR accumulate in circulating blood cells of mammals, in particular human beings affected by a tumor.

Thus antibodies directed against the human follicle-stimulating hormone receptor (FSHR), or antigen-binding portion thereof according to the invention may be used in immunochemical studies, for example in immunoprecipitation, western blotting, ELISA, immunocytochemical studies, for example confocal microscopy, immune electron microscopy, and/or immunohistochemical studies.

The present invention also provides antibodies against the human follicle-stimulating hormone receptor (FSHR), or antigen-binding portion thereof for use in an in vitro or in vivo diagnostic or imaging method.

In the present the in vitro or in vivo diagnostic or imaging method may be any method known to one skilled in the art in which an antibody or antigen-binding portion thereof could be used. For example in vivo diagnostic or imaging method may be selected from the group comprising Single Photon Emission Computed Tomography (SPECT), Positron Emission Tomography (PET), Contrast enhanced ultrasound imaging, and Magnetic Resonance Imaging (MRI) by using for example Mangradex nanoparticles.

Another object of the present invention is the in vitro use of an antibody against the human follicle-stimulating hormone receptor (FSHR), or antigen-binding portion thereof, for detecting cancerous cells, for example circulating FSHR-positive epithelial cancer cells, tumoral endothelial cells and/or the circulating FSHR ectodomain, in a sample.

The antibody against the human follicle-stimulating hormone receptor (FSHR), or antigen-binding portion thereof is defined as above.

In the present the sample may be a biological sample. The biological sample may be any biological sample known to one skilled in the art. The biological sample may for example be a liquid or solid sample. According to the invention, the sample may be any biological fluid, for example it can be a sample of blood, plasma, serum, urine, tissue, for example muscle, or a sample from a tissue biopsy.

In the present the cancerous cells may be any cancerous cells which express the follicle-stimulating hormone receptor (FSHR) known to one skilled in the art. It may be for example circulating FSHR-positive epithelial cancer cells, or tumoral endothelial cells.

In the present, the method for detecting cancer cells can be any detection method known to one skilled in the art. It may for example be Fluorescence-activated cell sorting (FACS) applied in flow cytometry.

In the present, the method for detecting circulating FSHR extracellular domain shed from the surface of FSHR-positive cancer cells and/or tumor endothelial cells can be any detection method known to one skilled in the art. It may be for example any immuno-enzymatic method known to one skilled in the art. For example it may be an ELISA [Vannier 1996 [15].

In the present, when the antibody against the human follicle-stimulating hormone receptor (hFSHR), or antigen-binding portion thereof is used in detection, diagnostic or imaging methods, the antibody may be labelled and/or tagged. For example the antibody against hFSHR or antigen-binding portion thereof may be tagged with any tag adapted and known to one skilled in the art. It may for example be a tag selected from the group comprising biotin, fluorescent dyes for example rhodopsin, Alexa-Fluor™, nanogold coated ligands, carbon-black coated ligands, mangradex, or a fluorescent ligand. For example the antibody against hFSHR, or antigen-binding portion thereof may be labelled and/or tagged with a compound selected from the group comprising radioactive molecules, for example comprising radioactive atoms for scintigraphic studies such as $^{123}$I, $^{124}$I, $^{111}$In, $^{186}$Re, $^{188}$Re, fluorochromes, invisible near infrared (NIR) compounds, for example NIR fluorescent IRDye™800-CW (Tanaka et al 2008 [30]), biotin.

In the present, when the antibody against the human follicle-stimulating hormone receptor (FSHR), or antigen-binding portion thereof is tagged it may be revealed with a conjugate molecule.

In the present, the conjugate molecule may be any molecule which binds to a tagged antibody against the human follicle-stimulating hormone receptor (FSHR), or antigen-binding portion thereof know from one in the art. For example, when the tag is biotin the conjugate molecule may be streptavidin.

In the present when the antibody against the human follicle-stimulating hormone receptor (FSHR), or antigen-binding portion thereof is labelled with radioisotopes and/or fluorochromes, it may be useful in imaging process, for example for detecting/localizing primary tumors and/or metastasis.

In the present when the antibody against the human follicle-stimulating hormone receptor (FSHR), or antigen-binding portion thereof is labelled with invisible near infrared (NIR) compounds, it may be useful in image-guided therapy.

Advantageously, the inventors have demonstrated that the antibody against the human follicle-stimulating hormone receptor (FSHR), or antigen-binding portion thereof, of the invention, for example due to its better affinity and specificity to the FSHR, allow to provide a better detection/results with regards to the presence or not of its receptor, for example in a sample.

In other words, the antibody against the human follicle-stimulating hormone receptor (FSHR), or antigen-binding portion thereof of the invention provide more reliable results and a better detection efficiency.

Thus the antibody against the human follicle-stimulating hormone receptor (FSHR), or antigen-binding portion thereof enable increased sensitivity of the method and, for example, the diagnostic prognosis.

Another object of the present invention is in vitro use of an antibody against the human follicle-stimulating hormone receptor (FSHR), or antigen-binding portion thereof, for monitoring the efficacy of anti-tumor agent for example by sequential imaging of the tumor size with an antibody against the human follicle-stimulating hormone receptor (FSHR), or antigen-binding portion thereof of the present invention.

In the present, the anti-tumor agent may be any anti-tumor agent known to one skilled in the art, for example chemotherapy, radiotherapy.

Another object of the present invention is a method for monitoring the efficacy of anti-tumor agent and/or anti-tumor treatment in vitro comprising the following step:
  a) measurement of the tumor size (S1) with an antibody against the human follicle-stimulating hormone receptor (FSHR), or antigen-binding portion thereof on an image,
  b) measurement of the tumor size (S2) with an antibody against the human follicle-stimulating hormone receptor (FSHR), or antigen-binding portion thereof on an image after said treatment,
  c) comparison of the tumor size and calculation of a score (S) according to the following formula:
  d) S=S2/S1,
a value of S lesser than 1.08 indicating that the treatment is effective In the present, the measurement of the tumor size can be carried out on any image obtained from imaging method using antibodies against the human follicle-stimulating hormone receptor (FSHR), or antigen-binding portion thereof of the present invention. It may be for example an image obtained from any imaging method as mentioned above.

In the present an antibody against the human follicle-stimulating hormone receptor (FSHR), or fragment thereof according to the invention may be obtained from a nucleotide sequence.

A subject of the present invention is thus an isolated nucleotide sequence encoding an antibody against the human follicle-stimulating hormone receptor (FSHR), or fragment thereof according to the invention.

In the present a nucleotide sequence may code for an antibody against the human follicle-stimulating hormone receptor (FSHR), or fragment thereof, which may comprise at least one of the group comprising:

A variable heavy (VH) chain complementarity determining region (CDR)1 having the amino acid sequence XaXbXcXdXe (SEQ ID NO 16) wherein Xa is Q, R or K; Xb is F, Q, S or Y, Xc is Y or W, Xd is V, L, I or T, and Xe is G, I, L, Q or T, A variable heavy (VH) chain complementarity determining region (CDR) 2 having the amino acid sequence EIXfPXgXhXiNTNYNEKFKG (SEQ ID NO 11) wherein Xf is F, L or Y, Xg is R or Q, Xh T or N and Xi G or Q, A variable heavy (VH) chain complementarity determining region (CDR) 3 having the amino acid sequence GPTASGYAMDY (SEQ ID NO 12).

One skilled in the art taking into consideration his technical knowledge and the amino acid sequence—nucleic acid translation code would be able to determine the corresponding nucleic acid coding sequence.

In the present invention, a nucleotide sequence coding the peptide sequence of the variable heavy (VH) chain complementarity determining region (CDR)1 of the isolated antibody directed against the human follicle-stimulating hormone receptor (FSHR), or antigen-binding portion thereof may be a selected from the group comprising CAGTTTTATGTGGGT (SEQ ID NO 39), CGGCAGTGGGTTATT (SEQ ID NO 40), AAGCAGTGGTTGTTG (SEQ ID NO 41), CGTTCGTGGATTCTG (SEQ ID NO 42), AAGCAGTGGTTGTTG (SEQ ID NO 43).

In the present invention, a nucleotide sequence coding the peptide sequence of the variable heavy (VH) chain complementarity determining region (CDR)2 of the isolated antibody directed against the human follicle-stimulating hormone receptor (FSHR), or antigen-binding portion thereof may be a selected from the group comprising GAAATTTTTCCTAGGACGGGTAACACCAACTACAACGAAAAATTCAAA GG (SEQ ID NO 44), GAAATTTTGCCGAGAAACGGTAACACCAACTACAACGAAAAATTCAAA GG (SEQ ID NO 45), GAAATTTTTCCGCGGAACGGGAACACCAACTACAACGAAAAATTCAAA GGC (SEQ ID NO 46), GAAATTTATCCGTAGAACTAGAACACCAACTACAACGAAAAATTCAAA GGC (SEQ ID NO 47), CGAAATTTATCCGCGGAACGGGAACACCAACTACAACGAAAAATTCAA AGG (SEQ ID NO 48).

In the present invention, a nucleotide sequence coding the peptide sequence of the variable heavy (VH) chain complementarity determining region (CDR)3 of the isolated antibody directed against the human follicle-stimulating hormone receptor (FSHR), or antigen-binding portion thereof may be GGCCCGACCGCGAGCGGCTATGCGATGGACTAC (SEQ ID NO 49).

By way of non limiting example, nucleotide sequences coding for peptide sequence SEQ ID NO 17-21 of the variable heavy (VH) of the isolated antibody directed against the human follicle-stimulating hormone receptor (FSHR), derived from the antibody against the human follicle-stimulating hormone receptor (FSHR) of the invention have been determined, and the corresponding peptide sequences deduced, and are presented respectively in table 2 below.

TABLE 2 nucleic acid coding for peptide of the variable heavy chain

| SEQ ID | Nucleic acid sequence |
|---|---|
| 28 | CAGGTTCAGCTGCAGCAGTCTGGCGCGGAACTGATGAAA CCGGGCGCGAGCGTGAAAATTTCCTGCAAAGCGACCGGC TACACCTTCAGCCAGTTTTATGTGGGTTGGGTGAAACAGC GCCCGGGTCATGGCCTGGAATGGATTGGCGAAATTTTTCC TAGGACGGGTAACACCAACTACAACGAAAAATTCAAAGGC AAAGCCACCTTCACCGCAGATACCTCCTCCAGCACCGCCT ACATGCAGCTGAGCAGCCTGACCTCTGAAGACTCTGCGG TGTATTACTGTGCAAGAGGCCCGACCGCGAGCGGCTATG CGATGGACTACTGGGGTCAGGGCACCTCTGTGACCGTGT CCTCT |
| 29 | CAGGTTCAGCTGCAGCAGTCTGGCGCGGAACTGATGAAA CCGGGCGCGAGCGTGAAAATTTCCTGCAAAGCGACCGGC TACACCTTCAGCCGGCAGTGGGTTATTTGGGTGAAACAGC GCCCGGGTCATGGCCTGGAATGGATTGGCGAAATTTTGC CGAGAAACGGTAACACCAACTACAACGAAAAATTCAAAGG CAAAGCCACCTTCACCGCAGATACCTCCTCCAGCACCGC CTACATGCAGCTGAGCAGCCTGACCTCTGAAGACTCTGC GGTGTATTACTGTGCAAGAGGCCCGACCGCGAGCGGCTA TGCGATGGACTACTGGGGTCAGGGCACCTCTGTGACCGT GTCCTCT |
| 30 | CAGGTTCAGCTGCAGCAGTCTGGCGCGGAACTGATGAAA CCGGGCGCGAGCGTGAAAATTTCCTGCAAAGCGACCGGC TACACCTTCAGCAAGCAGTGGTTGTTGTGGGTGAAACAGC GCCCGGGTCATGGCCTGGAATGGATTGGCGAAATTTTTCC GCGGAACGGGAACACCAACTACAACGAAAAATTCAAAGG CAAAGCCACCTTCACCGCAGATACCTCCTCCAGCACCGC CTACATGCAGCTGAGCAGCCTGACCTCTGAAGACTCTGC GGTGTATTACTGTGCAAGAGGCCCGACCGCGAGCGGCTA TGCGATGGACTACTGGGGTCAGGGCACCTCTGTGACCGT GTCCTCT |
| 31 | CAGGTTCAGCTGCAGCAGTCTGGCGCGGAACTGATGAAA CCGGGCGCGAGCGTGAAAATTTCCTGCAAAGCGACCGGC TACACCTTCAGCCGTTCGTGGATTCTGTGGGTGAAACAGC GCCCGGGTCATGGCCTGGAATGGATTGGCGAAATTTATC CGTAGAACTAGAACACCAACTACAACGAAAAATTCAAAGG CAAAGCCACCTTCACCGCAGATACCTCCTCCAGCACCGC CTACATGCAGCTGAGCAGCCTGACCTCTGAAGACTCTGC GGTGTATTACTGTGCAAGAGGCCCGACCGCGAGCGGCTA TGCGATGGACTACTGGGGTCAGGGCACCTCTGTGACCGT GTCCTCT |
| 32 | CAGGTTCAGCTGCAGCAGTCTGGCGCGGAACTGATGAAA CCGGGCGCGAGCGTGAAAATTTCCTGCAAAGCGACCGGC TACACCTTCAGCAAGTATTGGACTCAGTGGGTGAAACAGC GCCCGGGTCATGGCCTGGAATGGATTGGCGAAATTTATC CGCGGAACGGGAACACCAACTACAACGAAAAATTCAAAG GCAAAGCCACCTTCACCGCAGATACCTCCTCCAGCACCG CCTACATGCAGCTGAGCAGCCTGACCTCTGAAGACTCTGC GGTGTATTACTGTGCAAGAGGCCCGACCGCGAGCGGCTA TGCGATGGACTACTGGGGTCAGGGCACCTCTGTGACCGT GTCCTCT |

In the present invention, a nucleotide sequence coding the peptide sequence SEQ ID NO 17-21 of the variable heavy (VH) of the isolated antibody directed against the human follicle-stimulating hormone receptor (FSHR), or antigen-binding portion thereof may be a selected from the group comprising SEQ ID NO 28, SEQ ID NO 29, SEQ ID NO 30, SEQ ID NO 31, SEQ ID NO 32.

In the present invention, a nucleotide sequence coding the peptide sequence of the variable light (VL) chain complementarity determining region (CDR)1 of the isolated antibody directed against the human follicle-stimulating hormone receptor (FSHR), or antigen-binding portion thereof may be a selected from the group comprising nucleotide of sequence AGATCTAGTCAGAGCATTGTACATAGAAATGGAAACACTT ATTTAGAA (SEQ ID NO 24) or variant thereof In the present invention, a nucleotide sequence coding the peptide sequence of the variable light (VL) chain complementarity determining region (CDR)2 of the isolated antibody directed against the human follicle-stimulating hormone receptor (FSHR), or antigen-binding portion thereof may be a nucleotide comprising nucleotide of sequence AAAGTTTCCAACCGATTTTCT (SEQ ID NO 25) or variant thereof.

In the present invention, a nucleotide sequence coding the peptide sequence of the light chain (VL) complementarity determining region (CDR)3 of the isolated antibody directed against the human follicle-stimulating hormone receptor (FSHR), or antigen-binding portion thereof may be a selected from the group comprising nucleotide of sequence TTTCAAGGTTCACATGTTCCATTCACG (SEQ ID NO 26) or variant thereof.

In the present invention, a nucleotide sequence coding the peptide sequence selected from the group comprising the peptide of sequence SEQ ID NO 13-15, 22 of the variable light (VL) chain of the isolated antibody directed against the human follicle-stimulating hormone receptor (FSHR), or antigen-binding portion thereof may be a selected from the group comprising nucleotides of sequence SEQ ID NO 23, SEQ ID NO 24, SEQ ID NO 25 and SEQ ID NO 26.

A subject of the present invention is also a recombinant vector, in particular an expression vector, comprising a nucleotide sequence according to the invention.

By way of nonlimiting example, the nucleotide sequences of the constant region of the heavy chain derived from the antibody against the human follicle-stimulating hormone receptor (FSHR) of the invention have been determined, and the corresponding peptide sequences deduced, and are presented respectively in table 3 below.

TABLE 3 nucleic acid coding for the constant part of heavy chain

| SEQ ID | Nucleic acid sequence |
|---|---|
| 34 | ATGGGCTGGTCCTGCATCATCCTGTTTCTGGTGGCCACCG CCACAGGCGTCCACTCTCAGGTGCAGCTGCAGCAGTCCG GCGCCGAACTGATGAAGCCTGGCGCCTCCGTGAAGATCT CCTGCAAGGCCACCGGATACACCTTCTCCCAGTTCTACGT GGGCTGGGTGAAGCAGAGGCCTGGCCACGGACTGGAGT GGATCGGCGAGATCTTCCCCGGACCGGCAACACCAACT ACAACGAGAAGTTCAAGGGCAAGGCCACCTTCACCGCCG ACACCTCCTCCAGCACCGCCTACATGCAGCTGTCCTCCCT GACCTCCGAGGACTCCGCCGTGTACTACTGCGCTAGGGG CCCTACAGCTTCCGGCTACGCCATGGACTACTGGGGACA GGGCACCTCCGTGACCGTGTCCTCCGCTAAAACAACAGC CCCATCGGTCTATCCACTGGCCCCTGTGTGTGGAGATACA ACTGGCTCCTCGGTGACTCTAGGATGCCTGGTCAAGGGT TATTTCCCTGAGCCAGTGACCTTGACCTGGAACTCTGGAT CCCTGTCCAGTGGTGTGCACACCTTCCCAGCTGTCCTGCA GTCTGACCTCTACACCCTCAGCAGCTCAGTGACTGTAACC TCGAGCACCTGGCCCAGCCAGTCCATCACCTGCAATGTG GCCCACCCGGCAAGCAGCACCAAGGTGGACAAGAAATT GAGCCCAGAGGGCCCACAATCAAGCCCTGTCCTCCATGC AAATGCCCAGCACCTAACCTCTTGGGTGGACCATCCGTCT TCATCTTCCCTCCAAAGATCAAGGATGTACTCATGATCTCC CTGAGCCCCATAGTCACATGTGTGGTGGTGGATGTGAGC GAGGATGACCCAGATGTCCAGATCAGCTGGTTTGTGAACA ACGTGGAAGTACACACAGCTCAGACACAAACCCATAGAGA GGATTACAACAGTACTCTCCGGGTGGTCAGTGCCCTCCC CATCCAGCACCAGGACTGGATGAGTGGCAAGGAGTTCAA ATGCAAGGTCAACAACAAAGACCTCCCAGCGCCCATCGA GAGAACCATCTCAAAACCCAAAGGGTCAGTAAGAGCTCCA CAGGTATATGTCTTGCCTCCACCAGAAGAAGAGATGACTA AGAAACAGGTCACTCTGACCTGCATGGTCACAGACTTCAT GCCTGAAGACATTTACGTGGAGTGGACCAACAACGGGAA AACAGAGCTAAACTACAAGAACACTGAACCAGTCCTGGAC |

TABLE 3-continued nucleic acid coding for the constant part of heavy chain

| SEQ ID | Nucleic acid sequence |
|---|---|
| | TCTGATGGTTCTTACTTCATGTACAGCAAGCTGAGAGTGG AAAAGAAGAACTGGGTGGAAAGAAATAGCTACTCCTGTTC AGTGGTCCACGAGGGTCTGCACAATCACCACACGACTAA GAGCTTCTCCCGGACTCCGGGTAAA |
| 35 | ATGGGCTGGTCCTGCATCATCCTGTTTCTGGTGGCCACCG CCACAGGCGTCCACTCTCAGGTGCAGCTGCAGCAGTCCG GCGCTGAGCTGATGAAGCCTGGCGCCTCCGTGAAGATCT CCTGCAAGGCCACCGGCTACACCTTCTCCAGGCAGTGGG TGATCTGGGTGAAGCAGAGGCCTGGACACGGCCTGGAGT GGATCGGCGAGATCCTGCCCCGGAACGGCAACACCAACT ACAACGAAAAGTTCAAGGGCAAGGCCACCTTCACCGCCG ACACCTCCTCCTCCACCGCCTACATGCAGCTGTCCTCCCT GACCTCCGAGGACTCCGCCGTGTACTACTGTGCTAGGGG CCCTACCGCCTCCGGCTATGCCATGGACTACTGGGGCCA GGGCACATCCGTGACCGTGTCCTCCGCTAAAACAACAGC CCCATCGGTCTATCCACTGGCCCCTGTGTGTGGAGATACA ACTGGCTCCTCGGTGACTCTAGGATGCCTGGTCAAGGGT TATTTCCCTGAGCCAGTGACCTTGACCTGGAACTCTGGAT CCCTGTCCAGTGGTGTGCACACCTTCCCAGCTGTCCTGCA GTCTGACCTCTACACCCTCAGCAGCTCAGTGACTGTAACC TCGAGCACCTGGCCCAGCCAGTCCATCACCTGCAATGTG GCCCACCCGGCAAGCAGCACCAAGGTGGACAAGAAATT GAGCCCAGAGGGCCCACAATCAAGCCCTGTCCTCCATGC AAATGCCCAGCACCTAACCTCTTGGGTGGACCATCCGTCT TCATCTTCCCTCCAAAGATCAAGGATGTACTCATGATCTCC CTGAGCCCCATAGTCACATGTGTGGTGGTGGATGTGAGC GAGGATGACCCAGATGTCCAGATCAGCTGGTTTGTGAACA ACGTGGAAGTACACACAGCTCAGACACAAACCCATAGAGA GGATTACAACAGTACTCTCCGGGTGGTCAGTGCCCTCCC CATCCAGCACCAGGACTGGATGAGTGGCAAGGAGTTCAA ATGCAAGGTCAACAACAAAGACCTCCCAGCGCCCATCGA GAGAACCATCTCAAAACCCAAAGGGTCAGTAAGAGCTCCA CAGGTATATGTCTTGCCTCCACCAGAAGAAGAGATGACTA AGAAACAGGTCACTCTGACCTGCATGGTCACAGACTTCAT GCCTGAAGACATTTACGTGGAGTGGACCAACAACGGGAA AACAGAGCTAAACTACAAGAACACTGAACCAGTCCTGGAC TCTGATGGTTCTTACTTCATGTACAGCAAGCTGAGAGTGG AAAAGAAGAACTGGGTGGAAAGAAATAGCTACTCCTGTTC AGTGGTCCACGAGGGTCTGCACAATCACCACACGACTAA GAGCTTCTCCCGGACTCCGGGTAAA |
| 36 | ATGGGCTGGTCCTGCATCATCCTGTTTCTGGTGGCCACCG CCACAGGCGTCCACTCTCAGGTGCAGCTGCAGCAGTCCG GCGCTGAGCTGATGAAGCCTGGCGCCTCCGTGAAGATCA GCTGCAAGGCCACCGGCTACACCTTCTCCAAGCAGTGGC TGCTGTGGGTGAAGCAGAGGCCTGGCCATGGCCTGGAGT GGATCGGCGAGATCTTCCCCCGGAACGGCAACACCAACT ACAACGAGAAGTTCAAGGGCAAGGCCACCTTCACCGCCG ACACCTCCTCCTCCACCGCCTACATGCAGCTGAGCTCCCT GACCTCCGAGGACTCCGCCGTGTACTACTGTGCTAGGGG ACCCACAGCCTCCGGCTACGCTATGGACTACTGGGGCCA GGGAACCTCCGTGACCGTGTCCTCCGCTAAAACAACAGC CCCATCGGTCTATCCACTGGCCCCTGTGTGTGGAGATACA ACTGGCTCCTCGGTGACTCTAGGATGCCTGGTCAAGGGT TATTTCCCTGAGCCAGTGACCTTGACCTGGAACTCTGGAT CCCTGTCCAGTGGTGTGCACACCTTCCCAGCTGTCCTGCA GTCTGACCTCTACACCCTCAGCAGCTCAGTGACTGTAACC TCGAGCACCTGGCCCAGCCAGTCCATCACCTGCAATGTG GCCCACCCGGCAAGCAGCACCAAGGTGGACAAGAAATT GAGCCCAGAGGGCCCACAATCAAGCCCTGTCCTCCATGC AAATGCCCAGCACCTAACCTCTTGGGTGGACCATCCGTCT TCATCTTCCCTCCAAAGATCAAGGATGTACTCATGATCTCC CTGAGCCCCATAGTCACATGTGTGGTGGTGGATGTGAGC GAGGATGACCCAGATGTCCAGATCAGCTGGTTTGTGAACA ACGTGGAAGTACACACAGCTCAGACACAAACCCATAGAGA GGATTACAACAGTACTCTCCGGGTGGTCAGTGCCCTCCC CATCCAGCACCAGGACTGGATGAGTGGCAAGGAGTTCAA ATGCAAGGTCAACAACAAAGACCTCCCAGCGCCCATCGA GAGAACCATCTCAAAACCCAAAGGGTCAGTAAGAGCTCCA CAGGTATATGTCTTGCCTCCACCAGAAGAAGAGATGACTA AGAAACAGGTCACTCTGACCTGCATGGTCACAGACTTCAT GCCTGAAGACATTTACGTGGAGTGGACCAACAACGGGAA AACAGAGCTAAACTACAAGAACACTGAACCAGTCCTGGAC TCTGATGGTTCTTACTTCATGTACAGCAAGCTGAGAGTGG |

TABLE 3-continued nucleic acid coding for the constant part of heavy chain

| SEQ ID | Nucleic acid sequence |
|---|---|
|  | AAAAGAAGAACTGGGTGGAAAGAAATAGCTACTCCTGTTC<br>AGTGGTCCACGAGGGTCTGCACAATCACCACACGACTAA<br>GAGCTTCTCCCGGACTCCGGGTAAA |
| 37 | ATGGGCTGGTCCTGCATCATCCTGTTTCTGGTGGCCACCG<br>CCACAGGCGTCCACTCTCAGGTGCAGCTGCAGCAGTCCG<br>GAGCCGAGCTGATGAAGCCTGGCGCCTCCGTGAAGATCA<br>GCTGCAAGGCCACCGGCTACACCTKHCCAGGTCCTGGA<br>TCCTGTGGGTGAAGCAGAGGCCTGGCCACGGACTGGAGT<br>GGATCGGCGAGATCTACCCCCAGAACCAGAACACCAACT<br>ACAACGAGAAGTTCAAGGGCAAGGCCACCTTCACCGCCG<br>ACACCTCCTCCTCCACCGCCTACATGCAGCTGTCCTCCCT<br>GACCTCCGAGGACAGCGCCGTGTACTACTGCGCTAGGGG<br>CCCTACCGCTTCCGGCTATGCCATGGACTACTGGGGCCA<br>GGGCACATCCGTGACCGTGTCCTCCGCTAAAACAACAGC<br>CCCATCGGTCTATCCACTGGCCCCTGTGTGTGGAGATACA<br>ACTGGCTCCTCGGTGACTCTAGGATGCCTGGTCAAGGGT<br>TATTTCCCTGAGCCAGTGACCTTGACCTGGAACTCTGGAT<br>CCCTGTCCAGTGGTGTGCACACCTTCCCAGCTGTCCTGCA<br>GTCTGACCTCTACACCCTCAGCAGCTCAGTGACTGTAACC<br>TCGAGCACCTGGCCCAGCCAGTCCATCACCTGCAATGTG<br>GCCCACCCGGCAAGCAGCACCAAGGTGGACAAGAAAATT<br>GAGCCGAGAGGGCCCACAATCAAGCCCTGTCCTCCATGC<br>AAATGCCCAGCACCTAACCTCTTGGGTGGACCATCCGTCT<br>TCATCTTCCCTCCAAAGATCAAGGATGTACTCATGATCTCC<br>CTGAGCCCCATAGTCACATGTGTGGTGGTGGATGTGAGC<br>GAGGATGACCCAGATGTCCAGATCAGCTGGTTTGTGAACA<br>ACGTGGAAGTACACACAGCTCAGACACAAACCCATAGAGA<br>GGATTACAACAGTACTCTCCGGGTGGTCAGTGCCCTCCC<br>CATCCAGCACCAGGACTGGATGAGTGGCAAGGAGTTCAA<br>ATGCAAGGTCAACAACAAAGACCTCCCAGCGCCCATCGA<br>GAGAACCATCTCAAAACCCAAAGGGTCAGTAAGAGCTCCA<br>CAGGTATATGTCTTGCCTCCACCAGAAGAAGAGATGACTA<br>AGAAACAGGTCACTCTGACCTGCATGGTCACAGACTTCAT<br>GCCTGAAGACATTTACGTGGAGTGGACCAACAACGGGAA<br>AACAGAGCTAAACTACAAGAACACTGAACCAGTCCTGGAC<br>TCTGATGGTTCTTACTTCATGTACAGCAAGCTGAGAGTGG<br>AAAAGAAGAACTGGGTGGAAAGAAATAGCTACTCCTGTTC<br>AGTGGTCCACGAGGGTCTGCACAATCACCACACGACTAA<br>GAGCTTCTCCCGGACTCCGGGTAAA |
| 38 | ATGGGCTGGTCCTGCATCATCCTGTTTCTGGTGGCCACCG<br>CCACAGGCGTCCACTCTCAGGTGCAGCTGCAGCAGTCCG<br>GCGCTGAGCTGATGAAGCCCGGCGCTTCCGTGAAGATCT<br>CCTGCAAGGCCACCGGCTACACCTTCAGCAAGTACTGGA<br>CCCAGTGGGTGAAGCAGAGGCCCGGACACGGACTGGAG<br>TGGATCGGCGAGATCTACCCCAGGAACGGCAACACCAAC<br>TACAACGAGAAGTTCAAGGGCAAGGCCACCTTCACCGCC<br>GACACATCCTCCTCCACCGCCTACATGCAGCTGTCCTCCC<br>TGACCTCCGAGGACTCCGCCGTGTACTACTGTGCTAGGG<br>GCCCTACCGCCTCCGGCTATGCCATGGACTACTGGGGCC<br>AGGGCACATCCGTGACCGTGTCCAGCGCTAAAACAACAG<br>CCCCATCGGTCTATCCACTGGCCCCTGTGTGTGGAGATAC<br>AACTGGCTCCTCGGTGACTCTAGGATGCCTGGTCAAGGG<br>TTATTTCCCTGAGCCAGTGACCTTGACCTGGAACTCTGGA<br>TCCCTGTCCAGTGGTGTGCACACCTTCCCAGCTGTCCTGC<br>AGTCTGACCTCTACACCCTCAGCAGCTCAGTGACTGTAAC<br>CTCGAGCACCTGGCCCAGCCAGTCCATCACCTGCAATGT<br>GGCCCACCCGGCAAGCAGCACCAAGGTGGACAAGAAAT<br>TGAGCCCAGAGGGCCCACAATCAAGCCCTGTCCTCCATG<br>CAAATGCCCAGCACCTAACCTCTTGGGTGGACCATCCGTC<br>TTCATCTTCCCTCCAAAGATCAAGGATGTACTCATGATCTC<br>CCTGAGCCCCATAGTCACATGTGTGGTGGTGGATGTGAG<br>CGAGGATGACCCAGATGTCCAGATCAGCTGGTTTGTGAAC<br>AACGTGGAAGTACACACAGCTCAGACACAAACCCATAGAG<br>AGGATTACAACAGTACTCTCCGGGTGGTCAGTGCCCTCCC<br>CATCCAGCACCAGGACTGGATGAGTGGCAAGGAGTTCAA<br>ATGCAAGGTCAACAACAAAGACCTCCCAGCGCCCATCGA<br>GAGAACCATCTCAAAGATCAAAGGGTCAGTAAGAGCTCCA<br>CAGGTATATGTCTTGCCTCCACCAGAAGAAGAGATGACTA<br>AGAAACAGGTCACTCTGACCTGCATGGTCACAGACTTCAT<br>GCCTGAAGACATTTACGTGGAGTGGACCAACAACGGGAA<br>AACAGAGCTAAACTACAAGAACACTGAACCAGTCCTGGAC<br>TCTGATGGTTCTTACTTCATGTACAGCAAGCTGAGAGTGG<br>AAAAGAAGAACTGGGTGGAAAGAAATAGCTACTCCTGTTC<br>AGTGGTCCACGAGGGTCTGCACAATCACCACACGACTAA<br>GAGCTTCTCCCGGACTCCGGGTAAA |

Another object of the present invention relates to an expression vector comprising the isolated nucleic acid or the nucleotide sequence coding an antibody against the human follicle-stimulating hormone receptor (FSHR), or fragment thereof.

The present invention relates also to an expression vector comprising an isolated nucleic acid or the nucleotide sequence selected from the group comprising SEQ ID NO 23, SEQ ID NO 24, SEQ ID NO 25, SEQ ID NO 26, SEQ ID NO 28, SEQ ID NO 29, SEQ ID NO 30, SEQ ID NO 31, SEQ ID NO 32.

In the present, the vector may be any one of the vectors known to those skilled in the art to produce recombinant proteins. It is generally chosen as a function of the cellular host used. The vector may for example be chosen from the vectors listed in the catalogs of any of the commercial suppliers like Promega®, QIAGEN® or SANTA CRUZ BIOTECHNOLGY®. It may be, for example, the expression vector described in document WO 83/004261 [34]. The vector may for example be selected from group comprising pcDNA3.1 expression vector, FJB IgG expression vectors.

Another object of the present invention relates to a host cell comprising a nucleic acid coding an antibody against the human follicle-stimulating hormone receptor (FSHR), or fragment thereof or an expression vector comprising a nucleic acid coding an antibody against the human follicle-stimulating hormone receptor (FSHR), or fragment thereof.

The nucleic acid or expression vector are as defined above.

The host cell may be any suitable host for the production of an antibody against the human follicle-stimulating hormone receptor (FSHR), or fragment thereof of the present from the aforementioned vectors comprising a nucleotide sequence encoding an antibody against the human follicle-stimulating hormone receptor (FSHR), or fragment thereof according to the invention.

For the purposes of the present invention, "host cell" is understood to mean a prokaryotic or eukaryotic cell. Host cells commonly used for expression of recombinant proteins include cells of bacteria such as *Escherichia coli* or *Bacillus* sp., Yeast cells such as *Saccharomyces cerevisiae*, fungal cells such as *Aspergillus Niger*, insect cells, and/or mammalian cells. The mammalian cells may be for example selected from the group comprising murine cells, human cells. It may be for example cells selected from the group comprising HEK 293, PER-C6, CHO cells, CAR-T cells, CAR-NK cells. In the present, the host cell may be a CHO cell.

The transformation of prokaryotic and eukaryotic cells is a process/technique well known to a person skilled in the art. The transformation may be carried out, for example by lipofection, Electroporation, heat shock, or chemical methods. Depending on the cell to be transformed, a person skilled in the art can easily determine the means necessary for the transformation of the selected host cell. Thus, the expression vector and the method of introducing the expression vector into the host cell will be selected in accordance with the selected host cell. The host cell transformed by an expression vector will produce a corresponding protein, for example in recombinant form. A person skilled in the art can readily verify that the host cell produces the protein, for example recombinant, for example using immunoprecipitation followed by the Western blotting technique.

An object of the present invention is also a method of producing an antibody against the human follicle-stimulating hormone receptor (FSHR) or antigen-binding portion thereof, of the present invention In the present the method of producing an antibody against the human follicle-stimulating hormone receptor (FSHR) or antigen-binding portion thereof may be carried out by any method known to one skilled in the art to produce an antibody or antigen-binding portion thereof. A method of producing an antibody against the human follicle-stimulating hormone receptor (FSHR) or antigen-binding portion thereof may comprise culturing a host cell according to the invention and recovering antibody or antigen-binding portion thereof from the cell culture.

The culture of a host cell may be carried out by any method known to one skilled in the art and adapted to the cell. Culture of prokaryotic and eukaryotic cells is a technique well known to those skilled in the art. Depending on the cell, a person skilled in the art may easily determine the necessary means, culture medium, time and temperature conditions required for the culture of the selected host cell.

The recovery of an antibody or antigen-binding portion thereof from the cell culture may be carried out by any method known to one skilled in the art. It may, for example, be a method selected among electrophoresis, ultracentrifugation, differential precipitation, ultrafiltration, membrane or gel filtration, affinity chromatography.

In the present, the antibody against the human follicle-stimulating hormone receptor (FSHR), or antigen-binding portion thereof of the invention may be produced by a hybridoma method, for example as described by Kohler and Milstein 1975 [35], the human B-cell hybridoma technique (Cote et al., 1983 [36]) and/or may be made by recombinant DNA methods, for example as disclosed in U.S. Pat. No. 4,816,567 [37]. The antibody or antigen-binding portion thereof of the invention may also be produced and isolated from phage antibody libraries using the techniques disclosed in Clackson et al 1991 [38] and Marks et al 1991 [39].

Other advantages may still be apparent to those skilled in the art by reading the examples below, illustrated by the accompanying figures, given by way of illustration.

BRIEF DESCRIPTION OF THE FIGURES

FIG. 2 is a diagram representing the results of FACS with 1": antibody with CDR 1 of SEQ ID NO 1 and with CDR 2 of SEQ ID NO 6, "2": antibody with CDR 1 of SEQ ID NO 2 and with CDR 2 of SEQ ID NO 7, "3": antibody with CDR 1 of SEQ ID NO 3 and with CDR 2 of SEQ ID NO 8, "4": antibody with CDR 1 of SEQ ID NO 4 and with CDR 2 of SEQ ID NO 9, "5": antibody with CDR 1 of SEQ ID NO 5 and with CDR 2 of SEQ ID NO 10, and all the CDR3 sequence is GPTASGYAMDY (SEQ ID NO 12) in the heavy chain, and the CDR1 sequence of RSSQSIVHRNGNTYLE (SEQ ID NO 13), the CDR 2 sequence of KVSNRFS (SEQ ID NO 14) and the CDR3 sequence of FQGSHVPFT (SEQ ID NO 15) in the light chain, "6" is an mouse IgG2A antibody (control) and "7" known antibody against human FSHR.

EXAMPLES

Example 1: Method of Manufacturing Antibody

1. Genes and Vectors

For the production of mouse IgG2a anti-huFSHR according the invention where only the heavy chain was randomized, the genes coding for the VH of five different anti human FSHR and the gene coding for the VK of a known FSHR antibody VK (SEQ ID NO 27) designed with BsmBI flanking regions for further cloning into FJB IgG expression vectors, were produced. The nucleotide sequences coding for heavy chain the five different anti human FSHR correspond respectively to sequences SEQ ID NO 28 to 32 in the sequence listing.

The obtained genes coding for the different VH domains were cloned separately via BsmBI a pcDNA3.1 expression vector in frame with the mouse IgG2a heavy chain constant domains encoding genes. These nucleotide sequences correspond to sequences SEQ ID NO 28 to 32 in the sequence listing. In parallel, the synthetic nucleic acid coding for the VK comprising SEQ ID NO 33 was cloned also via BsmBI restriction endonucleases into a pDNA3.1 expression vector in frame with mouse CK encoding gene.

The sequencing of the resulting expression vectors constructs confirmed that the cloned domains corresponded were cloned in frame with the mammal signal peptide and with the genes encoding for constant domains present in the FJB expression vectors.

2. Procedure

The Antibody expression system: Gibco™ ExpiCHO™ Expression System (ThermoFisher Scientific®; Cat No A29133, ExpiCHO™ Expression System Kit Gibco™) and ExpiCHO-S™ cells (ThermoFisher Scientific®; Cat No A29127) were used.

The Affinity chromatography system: protein A in an ÄKTA™ pure chromatography system (GE Healthcare Life Sciences; Cat No 17061801), Column equilibration Buffer: 1× Phosphate Buffer Saline (PBS), Elution buffer: 100 mM acetic acid and Neutralization buffer: 1M Tris buffer, pH8.8 were used.

Figure 1:
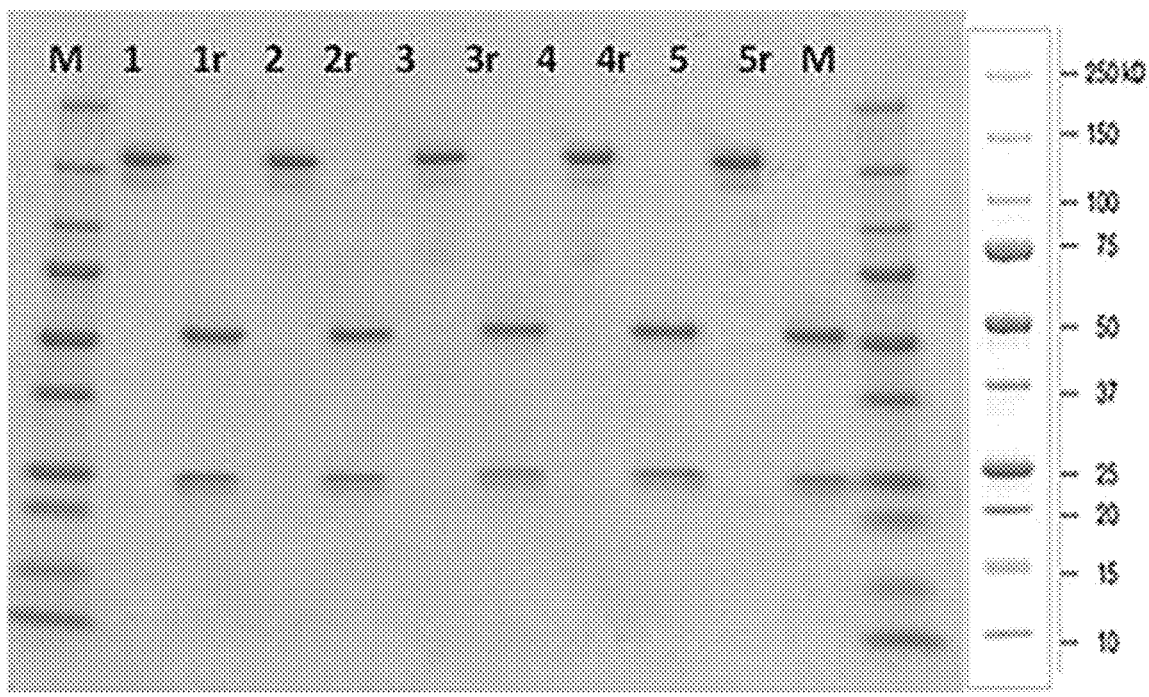
FIG. 1 is SDS-PAGE results of mouse IgG2a anti human FSHR produced in ExpiCHO™ cells (1 microgram of protein per lane). In this figure M means markers, r reduced, "1": antibody with CDR 1 of SEQ ID NO 1 and with CDR 2 of SEQ ID NO 6, "2": antibody with CDR 1 of SEQ ID NO 2 and with CDR 2 of SEQ ID NO 7, "3": antibody with CDR 1 of SEQ ID NO 3 and with CDR 2 of SEQ ID NO 8, "4": antibody with CDR 1 of SEQ ID NO 4 and with CDR 2 of SEQ ID NO 9, "5": antibody with CDR 1 of SEQ ID NO 5, and all the CDR3 sequence is GPTASGYAMDY (SEQ ID NO 12) in the heavy chain, and the CDR1 sequence of RSSQSIVHRNGNTYLE (SEQ ID NO 13), the CDR 2 sequence of KVSNRFS (SEQ ID NO 14) and the CDR3 sequence of FQGSHVPFT (SEQ ID NO 15) in the light chain.

The mouse IgG2 FSHR323 variants were produced by using the Gibco™ 19 ExpiCHO™ Expression System (ExpiCHO™ Expression System Kit Gibco™) according to manufacturer's instructions. The ExpiCHO™ cells were co-transfected with the heavy and light chain expression vectors and cultivated for 6-8 days in the in 500 ml of medium. After that the supernatants were collected and centrifuged at 10,000 g at 4° C. for 15 min. IgGs were purified via protein A in an ÄKTA™ pure chromatography system (GE Healthcare Life Sciences). The bound IgGs were eluted with 100 mM acetic acid (4 to 10-fold column volume), and fractions of ½ column volume were collected, neutralized with 1M Tris buffer, pH 8.8 (¼ of fraction volume), and stored at 4° C. The fractions containing the purified IgG were pooled, concentrated by centrifugation on a filter at 4° C. IgGs, dialyzed against 1×PBS (2 times, 2 h each at 4° C.), and finally sterilized by filtration at 0.22 µm. The total amounts and concentrations of the obtained IgGs are shown in table 1. The purity of produced IgGs has been determined by standard SDS-PAGE (12% acrylamide; 2 µg of antibody/lane; 100 V; 120 min migration time). The molecular weight markers used were ThermoFischer Scientific®, PageRuler™ Plus Prestained Protein Ladder (Cat No 26619) (5 µl/lane). Results showed that all IgG preparations were >95% pure and run with the expected molecular weight of 150 kDa under non-reducing, and 50 kDa and 25 kDa for the heavy chains and light chains, respectively in reducing conditions (i.e. 200 mM DTT) (FIG. 1).

TABLE 1

Amounts and concentration of mouse IgG2a anti human FSHR according to the invention produced in ExpiCHO cells.

| Sample | Concentration (mg/ml) | Volume (ml) | Amount (mg) |
| --- | --- | --- | --- |
| 1 | 1.5 | 32 | 53.3 |
| 2 | 1.3 | 33 | 40.7 |
| 3 | 1.1 | 31 | 33.1 |
| 4 | 2.1 | 33 | 67.1 |
| 5 | 2.1 | 19 | 39.9 |

In the above table "1": means antibody with CDR 1 of SEQ ID NO 1 and with CDR 2 of SEQ ID NO 6 in the heavy chain, "2": antibody with CDR 1 of SEQ ID NO 2 and with CDR 2 of SEQ ID NO 7 in the heavy chain, "3": antibody with CDR 1 of SEQ ID NO 3 and with CDR 2 of SEQ ID NO 8 in the heavy chain, "4": antibody with CDR 1 of SEQ ID NO 4 and with CDR 2 of SEQ ID NO 9 in the heavy chain, "5": antibody with CDR 1 of SEQ ID NO 5 and with CDR 2 of SEQ ID NO 10 in the heavy chain, the CDR3 sequence is GPTASGYAMDY (SEQ ID NO 12) in the heavy chain, and the CDR1 sequence of RSSQSIVHRNGNTYLE (SEQ ID NO 13), the CDR 2 sequence of KVSNRFS (SEQ ID NO 14) and the CDR3 sequence of FQGSHVPFT (SEQ ID NO 15) in the light chain.

Example 2: EC50 Determination of Mouse IgG2a Anti-huFSHR

In order to characterize and to check whether the IgGs anti human FSHR retain specificity for huFSHR and whether they bind to this receptor with higher affinity than known antibody, a binding FACS experiment using different IgGs (MABs) concentrations and huFSHR-L-cell and WT L_cells was performed. These cells were QCed for huFSHR expression.

In the present, HuFSHR L-cells (L cells stably expressing the human FSH-Receptor), WT L-cells (wild type L-cells; negative control) were used.

The HuFSHR L-cells were prepared as previously described [Vannier et al 1996 [15]. Briefly, mouse L cells were co-transfected, using the calcium phosphate precipitate method, with the plasmid encoding the hFSHR (pSG5-hFSHR) and with the plasmid pSV-Neo, a vector which confers resistance to the antibiotic G 418. Neomycin-resistant cells were selected in DMEM supplemented with 10% fetal calf serum and G 418 (geneticin, SIGMA-ALDRICH®) (1 mg/mL). The resistant clones were then screened for the hFSH receptor by an immunocytochemical test using the antireceptor antibody 323. The transfected cells were maintained in medium containing G 418 (200 ig/mL) for further studies. The samples were 4-fold serial dilution of monoclonal antibodies and buffer: FACS buffer (1×PBS containing 0.4 g/l human albumin, pH 7.4).

Procedure

Cells were diluted to a concentration of 1E+06 cells/ml in FACS buffer (1×PBS containing 0.4 g/L human albumin, pH 7.4) and 200 µl, corresponding to 2E+05 cells/well, were distributed in a 96 well U-bottom plate (ThermoFisher Scientific®; Cat No 168136, Nunc™ 96-Well).

Cells were pelleted, supernatant was discarded and 50 µl/well of each antibody dilutions were added to WT L-cells and huFSHR L-cells. Mix was incubated for 30 min at 4° C., gently shaking Cells were washed 3× with 150 µl/well of FACS buffer 100 µl/well of goat anti-mouse IgG conjugated to APC (GAM-APC) (BD™ Bioscience, 1:500 dilution) was added to the cells and incubated for 30 min at 4° C., gently shaking Cells were washed 3× with 150 µl/well of FACS Buffer Cell pellet was resuspended in 100 µl/well of FACS buffer MAB binding to cells was measured in FACS machine BD Accuri™ with a total of 10.000 events were acquired for each sample

The binding of the anti huFSHR mouse IgG2a to the L-cells was detected by using an antimouse IgG conjugated to APC (BD™ Bioscience).

Figure 2A:
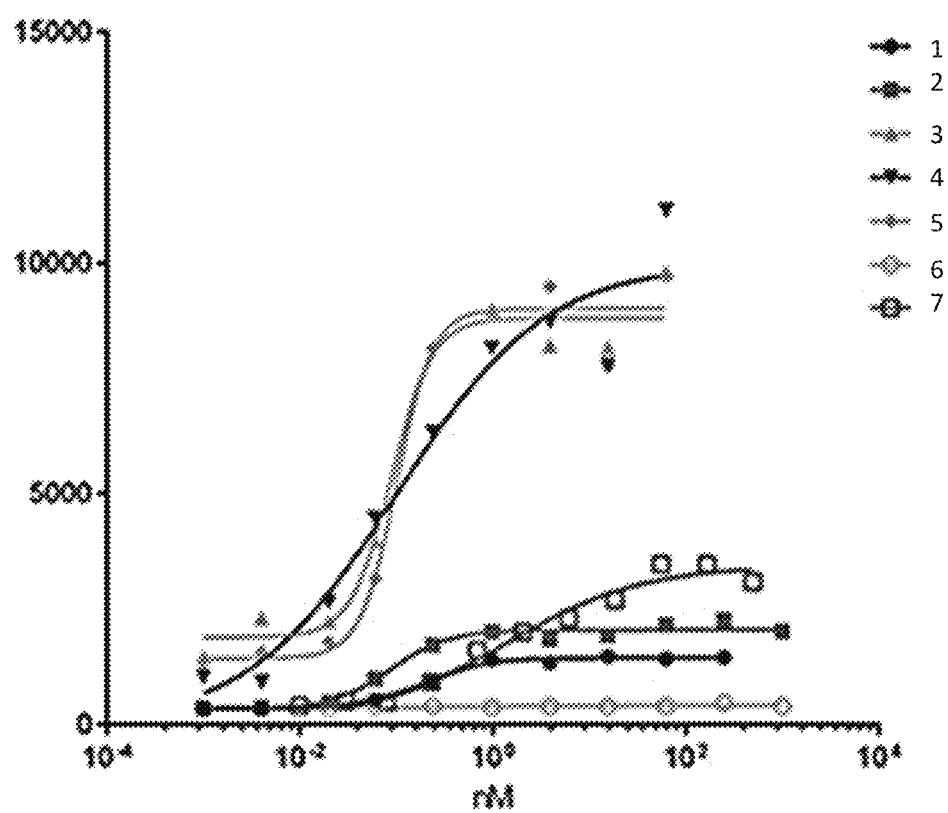
FIG. 2A represent a diagram obtained with HuFSHR L-cells (L cells stably expressing the human FSH-Receptor) and FIG. 2B represent a diagram obtained with WT L-cells (wild type L-cells; negative control).
Figure 2B:
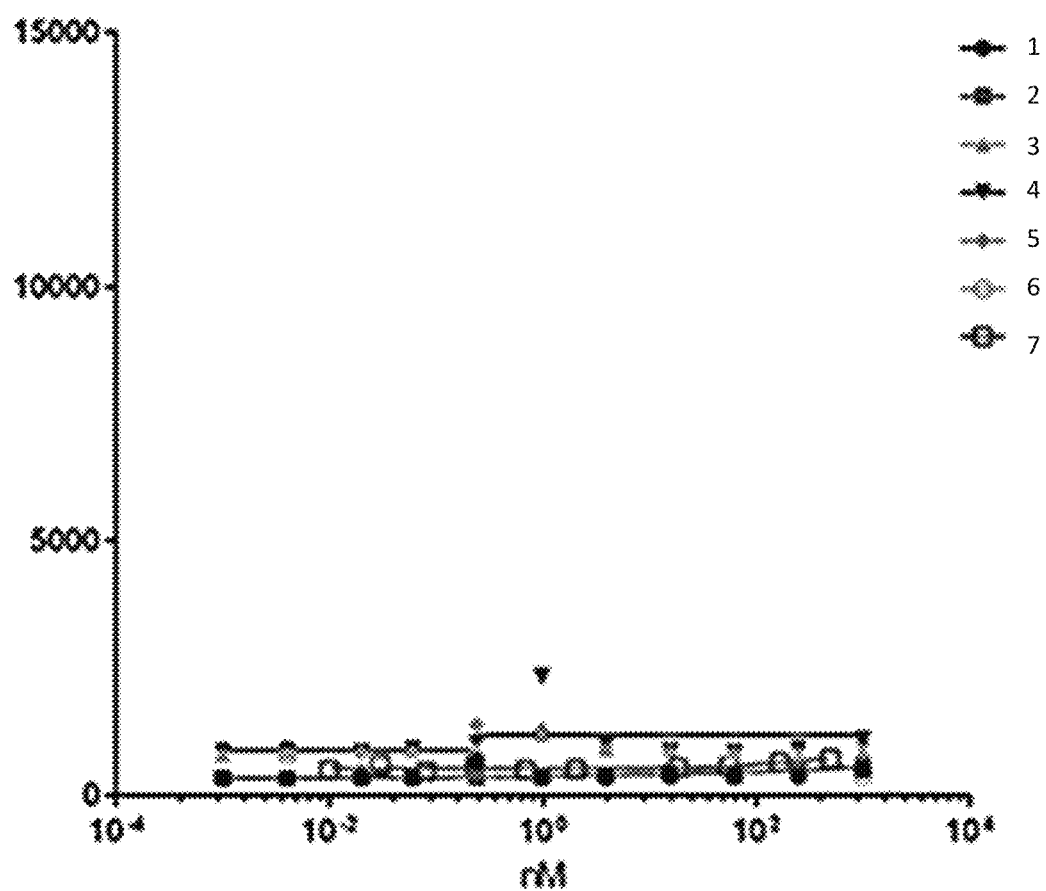

Results in FIG. 2 A showed that all antibodies according to the present invention retained the specific binding to huFSHR expressing cells with improved EC50 values (in the sub-nM range) compared to know anti-human FSHR antibody. In addition FIG. 2 B clearly demonstrate that examples of antibody according to the present invention were unable to bind WT L-cells (FIG. 2 B). In addition, results disclosed in table 2 below clearly demonstrate that examples of antibody according to the present invention have improved EC50 values (in the sub-nM range) compared to know anti-human FSHR antibody. In other words, these examples clearly demonstrate that the antibody of the present invention have EC 50 which are from 7.5 to 18.2-fold higher than that of a known antibody.

TABLE 2

EC50 values calculated for a known antibody and
mouse IgG2a anti-huFSHR of the present invention
in FACS binding experiment using huFSHR-L-cells

| Antibody | EC50 (nm) to huFSHR L-cells | EC50 (nm) to huFSHR L-cells |
|---|---|---|
| Known antibody | 1.582 | No binding |
| 1 | 0.2112 | No binding |
| 2 | 0.08678 | No binding |
| 3 | 0.08926 | No binding |
| 4 | 0.09802 | No binding |
| 5 | 0.1006 | No binding |

In the above table 2, "1" means antibody with CDR 1 of SEQ ID NO 1 and with CDR 2 of SEQ ID NO 6 in the heavy chain, "2": antibody with CDR 1 of SEQ ID NO 2 and with CDR 2 of SEQ ID NO 7 in the heavy chain, "3": antibody with CDR 1 of SEQ ID NO 3 and with CDR 2 of SEQ ID NO 8 in the heavy chain, "4": antibody with CDR 1 of SEQ ID NO 4 and with CDR 2 of SEQ ID NO 9 in the heavy chain, "5": antibody with CDR 1 of SEQ ID NO 5 and with CDR 2 of SEQ ID NO 10 in the heavy chain, the CDR3 sequence is GPTASGYAMDY (SEQ ID NO 12) in the heavy chain, and the CDR1 sequence of RSSQSIVHRNGNTYLE (SEQ ID NO 13), the CDR 2 sequence of KVSNRFS (SEQ ID NO 14) and the CDR3 sequence of FQGSHVPFT (SEQ ID NO 15) in the light chain.

Example 3: Determination of the Optimal Concentration of Mouse IgG2a Anti-huFSHR Antibodies for FSHR Detection by Standard Peroxidase Immunohistochemistry In order to determine the optimal concentration of antibodies when used in immunohistochemistry according to the invention, the following materials and methods have been used.

Materials and Methods

Chemicals: Sodium borohydride, 3-amino-9-ethylcarbazole (AEC), sodium azide, $H_2O_2$ 30%, goat serum, and hematoxylin Gill solution no 3 were purchased from SIGMA-ALDRICH®, Saint-Quentin Fallavier, France. Shandon ImmuMount medium was obtained from ThermoFisher Scientific®, Asniere sur Seine, France.

Immunohistochemistry: Serial 3-μm-thick sections of human testis tissue (n=30 sections) were cut, attached to SuperFrost slides, deparaffinized with xylene, dehydrated gradually in ethanol and washed with running tap water for 60 min. Access to tissue antigen sites for antibody attachment was enhanced by incubating slides at 90° C. for 40 min with 10 mM citrate buffer, pH 6. After cooling at room temperature (RT) for 20 min, and after each subsequent step, slides were rinsed with PBS. To block endogenous peroxidase activity, the sections were incubated with 6% hydrogen peroxide (15 min at RT, i.e. 20° C.). Sodium borohydride (10 mg/ml PBS) was used to quench free aldehyde groups (15 min, RT i.e. 20° C.). Non-specific binding of antibodies was blocked by incubating slides with 2% goat serum in Phosphate Buffer Saline (PBS) (blocking buffer) at 20° C. (RT) for 2 h. The slides were incubated with serial dilutions of the monoclonal primary antibodies 4, 2, 3 (5 μg/ml-1 μg/ml-0.2 μg/ml-0.04 μg/ml of blocking buffer) in blocking buffer overnight at 4° C. The known FSHR323 antibody (INSERM-Transfert, Paris) was used as a positive IgG2a control. The mouse IgG2a from SIGMA-ALDRICH® was used as a negative control. The biotinylated goat anti-mouse IgG (Fc-specific) antibody (dilution 1:200), used as secondary antibody, was detected by using streptavidin coupled to horseradish peroxidase (dilution 1:500). AEC was the chromogen we used. The sections were washed in distilled water containing 0.1% sodium azide, counterstained with Gill's hematoxylin for 10 s, and mounted in Shandon ImmuMount medium.

Figure 3:
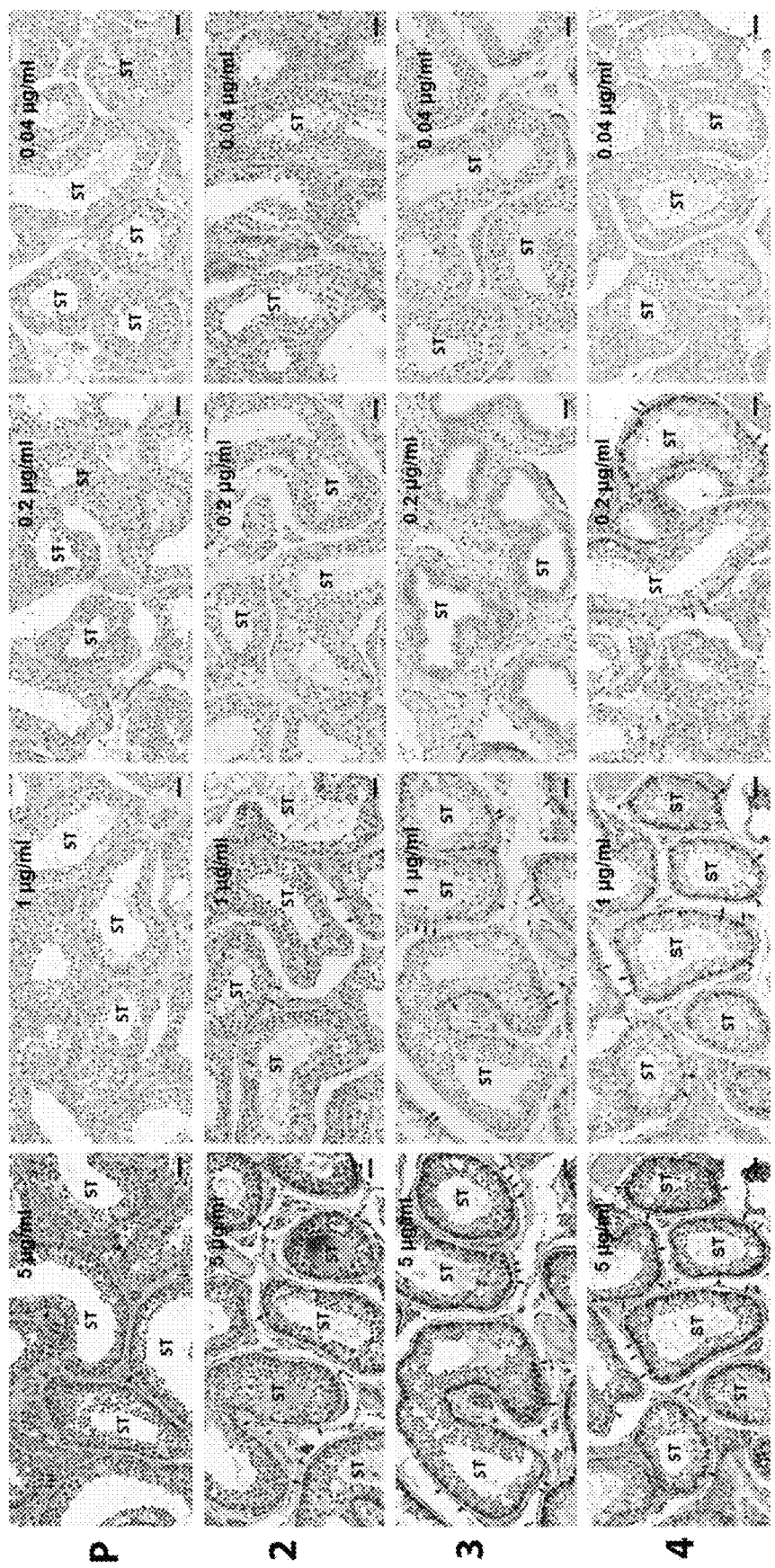
FIG. 3 is a photography of paraffin sections of human testis tissue after immunohistochemistry using known antibody against human FSHR ("P") or examples of antibody of the present invention ("2 to 4"). Immunohistochemical analysis was performed with the use of the anti-FSH-receptor monoclonal antibody 323, followed by a secondary biotinylated goat anti-mouse antibody visualized with the use of the streptavidin-peroxidase conjugate and aminoethyl carbazole as substrate. The sections were stained with hematoxylin. All arrows point to FSHR-positive Sertoli cells of the seminiferous tubules (ST), the physiological target cells of FSH.

Results:

FIG. 3 represents the imaged obtained with the antibodies 4, 2, 3 of the invention and the known FSHR323 antibody ("P"). FIG. 3 clearly demonstrate that the antibodies of the invention, when used in immunohistochemistry, have higher affinity than the known FSHR323 antibody. In other words, the antibodies of the present provide a better and more precise identification of the hFSHR.

In addition, as demonstrated on FIG. 3, the affinity of antibody of the invention, in particular antibody 4, 2, and 3 was from 5 to 25-fold higher than that of known antibody FSHR323 when tested for FSHR expression by immunohistochemistry (IHC) on paraffin sections of human testis tissue (ex: the optimal dilution for antibody 4 was 0.2 μg/ml while the optimal dilution for FSHR323: 5 μg/ml) (FIG. 3).

Example 4: Detection of FSHR Expression with Mouse IgG2a Anti-huFSHR in Samples of Human Cancerous Tissues In the experiment, the antibody used was the antibody obtained in example 1 above with the variable heavy (VH) chain complementarity determining region (CDR)1 amino acid sequence is RSWIL (SEQ ID NO 4), the variable heavy (VH) chain complementarity determining region (CDR)2 amino acid sequence is EIYPQNQNTNYNEKFKG (SEQ ID NO 9), a variable heavy (VH) chain complementarity determining region (CDR) 3 having the amino acid sequence GPTASGYAMDY (SEQ ID NO 12) and a variable light chain (VL) complementarity determining region (CDR)1 having the amino acid sequence RSSQSIVHRNGNTYLE (SEQ ID NO 13), a variable light chain (VL) complementarity determining region (CDR)2 having the amino acid sequence KVSNRFS (SEQ ID NO 14) and a variable light chain (VL) complementarity determining region (CDR) 3 having the amino acid sequence FQGSHVPFT (SEQ ID NO 15).

Archived paraffin sections (3 μm thick) of human breast cancer tissue (n=35 patients from the Curie Hospital, Paris, France) and of human prostate cancer (n=50 patients from Lariboisière Hospital, Paris France) were cut, attached to SuperFrost slides, deparaffinized with xylene, dehydrated gradually in ethanol and washed with running tap water for 60 min. Access to tissue antigen sites for antibody attachment was enhanced by incubating slides at 90° C. for 40 min with 10 mM citrate buffer, pH 6. After cooling at 20° C. (room temperature (RT)) for 20 min, and after each subsequent step, slides were rinsed with Phosphate Buffer Saline (PBS). To endogenous peroxidase activity was blocked by incubating sections with 6% hydrogen peroxide (15 min at RT). Sodium borohydride (10 mg/ml PBS) was used to quench free aldehyde groups (15 min, RT). Non-specific binding of antibodies was blocked by incubating slides with 2% goat serum in PBS (blocking buffer) at RT for 2 h. The slides were incubated with the monoclonal primary antibody (dilution: 0.2 μg/ml blocking buffer) in blocking buffer overnight at 4° C. The known FSHR323 antibody (INSERM-Transfert, Paris) was used as a positive IgG2a control. The mouse IgG2a from SIGMA-ALDRICH® was used as a negative control. The biotinylated goat anti-mouse IgG (Fc-specific) antibody (dilution 1:200), used as secondary antibody, was detected by using streptavidin coupled to horseradish peroxidase (dilution 1:500). AEC was the chromogen we used. The sections were washed in distilled water containing 0.1% sodium azide, counterstained with Gill's hematoxylin for 10 s, and mounted in Shandon ImmuMount medium.

Results

Figure 4:
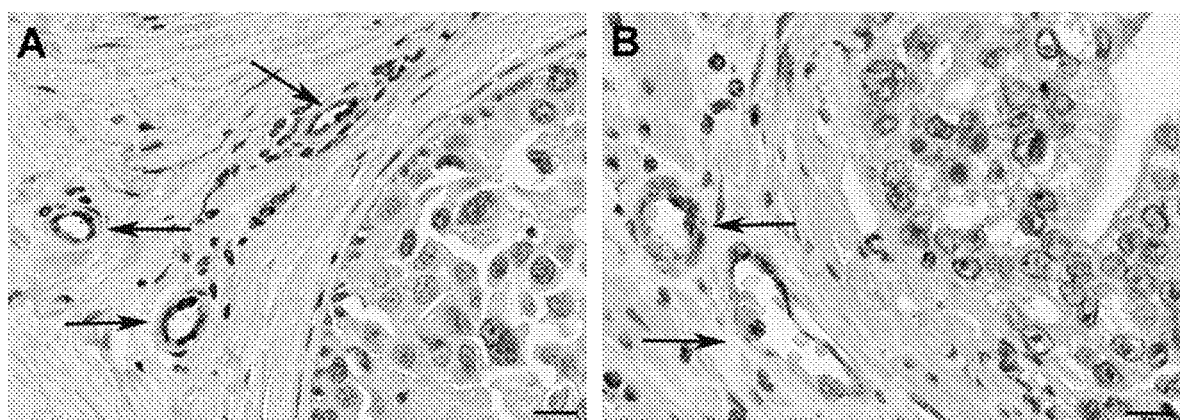
FIG. 4 is a photography of paraffin sections of human tissue from breast (A) and prostate (B). Arrows point to FSHR-positive vessels Bars: 50 μm.

FIG. 4 is a representative picture of the FSHR-expression on paraffin sections of human tissue from breast cancer and prostate cancer. As illustrated in this figure, the antibody 4 of the present invention allows to detect and identify the FSHR on vessels associated with breast cancer (A) and prostate cancer (B) (Arrows point to FSHR-positive blood vessels).

Example 5: Immunofluorescence Microscopy
Detection of FSHR Expression with Mouse IgG2a antihuFSHR in Cells Expressing the Receptor In order to determine a useful concentration of antibodies when used in immunofluorescence cytochemistry according to the invention, the following materials and methods have been used.

Materials and Methods

Chemicals: Ammonium chloride, 4,6-Diamidino-2-phenylindole dihydro-chloride (DAPI; #32670), and goat serum were purchased from SIGMA-ALDRICH®, Saint-Quentin Fallavier, France. Goat anti-mouse IgG-Alexa 555 (#A21137) and Shandon ImmuMount medium were obtained from ThermoFisher Scientific®, Asnieres sur Seine, France. Phosphate buffered saline (PBS)Dulbecco (#L182-10) was obtained from Biochrom Gmb, Berlin, Germany.

Immunofluorescence Microscopy

FSHR-L-cells and wild type L-cells were cultured at 37° C. on LabTeck 8-wells (10,000 cells/well) in DMEM containing 10% horse serum, 1 mM glutamine, 1 mM pyruvate in presence of 5% $CO_2$. When reached 70% confluence, the cells were washed with PBS (three times) and fixed with 4% paraformaldehyde in PBS (15 min at room temperature (RT)). The free aldehyde groups were quenched with 100 mM $NH_4Cl$ in PBS for 15 min at RT (i.e. 20° C.). To block the nonspecific binding of antibodies the cells were incubated 1 hour at RT (i.e. 20° C.) with PBS (pH=7.4) containing 2% goat serum (blocking buffer). FSHR was detected by incubating cells with serial dilutions of the monoclonal primary antibodies 1, 2, 3, 4, and 5 (3 µg/ml-1 µg/ml-0.3 µg/ml-0.1 µg/ml, 0.03 µg/ml, and 0.01 µg/ml of blocking buffer) overnight at 4° C. and with goat anti-mouse IgG-Alexa 555 (Invitrogen #A21137; dilution 1:1000 in blocking buffer) for 1 hour at room temperature. The known FSHR323 antibody (INSERM-Transfert, Paris) was used as a positive IgG2a control (3 µg/ml) as previously described in Radu et al. 2010 [9]. The cell nuclei were detected by incubating cells for 10 min with DAPI (SIGMA-ALDRICH®#32670; dilution 1:1000 in PBS). The slides were mounted in Dako fluorescent mounting medium containing 15 mM sodium azide and examined with an Olympus microscope. As negative controls wild type L-cells which do not express FSHR were used.

In the present example, the monoclonal primary antibodies 1, 2, 3, 4, and 5 means: "1": means antibody with CDR 1 of SEQ ID NO 1 and with CDR 2 of SEQ ID NO 6 in the heavy chain, "2": antibody with CDR 1 of SEQ ID NO 2 and with CDR 2 of SEQ ID NO 7 in the heavy chain, "3": antibody with CDR 1 of SEQ ID NO 3 and with CDR 2 of SEQ ID NO 8 in the heavy chain, "4": antibody with CDR 1 of SEQ ID NO 4 and with CDR 2 of SEQ ID NO 9 in the heavy chain, "5": antibody with CDR 1 of SEQ ID NO 5 and with CDR 2 of SEQ ID NO 10 in the heavy chain, the CDR3 sequence is GPTASGYAMDY (SEQ ID NO 12) in the heavy chain, and the CDR1 sequence of RSSQSIVHRNGNTYLE (SEQ ID NO 13), the CDR 2 sequence of KVSNRFS (SEQ ID NO 14) and the CDR3 sequence of FQGSHVPFT (SEQ ID NO 15) in the light chain.

Figure 5:
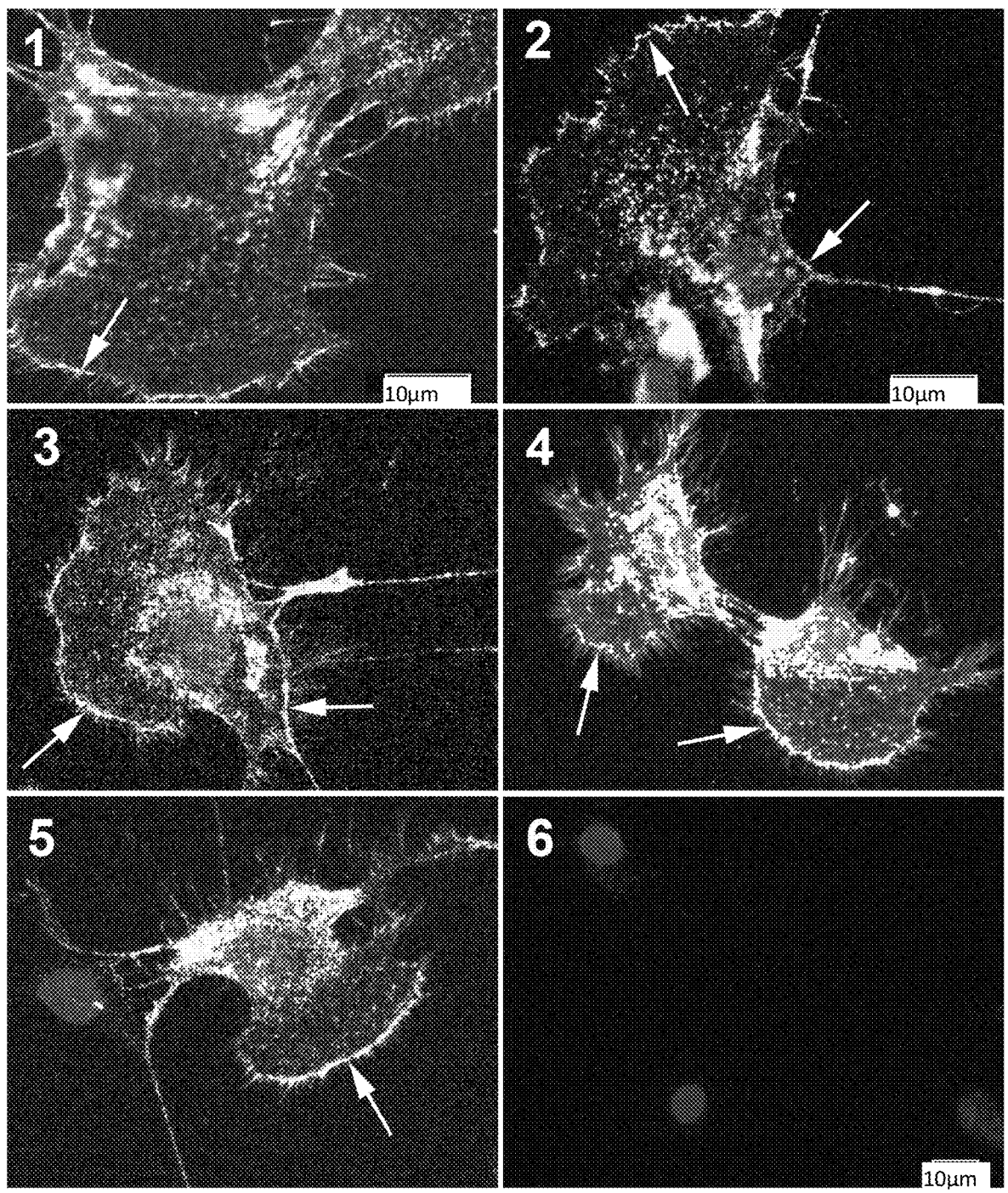
FIG. 5 are images obtained by Immunofluorescence microscopy. In this figure images are numbered according to the antibody used: "1": antibody with CDR 1 of SEQ ID NO 1 and with CDR 2 of SEQ ID NO 6, "2": antibody with CDR 1 of SEQ ID NO 2 and with CDR 2 of SEQ ID NO 7, "3": antibody with CDR 1 of SEQ ID NO 3 and with CDR 2 of SEQ ID NO 8, "4": antibody with CDR 1 of SEQ ID NO 4 and with CDR 2 of SEQ ID NO 9, "5": antibody with CDR 1 of SEQ ID NO 5, and all the CDR3 sequence is GPTASGYAMDY (SEQ ID NO 12) in the heavy chain, and the CDR1 sequence of RSSQSIVHRNGNTYLE (SEQ ID NO 13), the CDR 2 sequence of KVSNRFS (SEQ ID NO 14) and the CDR3 sequence of FQGSHVPFT (SEQ ID NO 15) in the light chain and "6" represent the image obtained with the known FSHR323 antibody.

Results in FIG. 5 showed that all five antibodies according to the present invention were able to detect specifically the huFSHR in cells stably expressing the receptor. In particular, the results demonstrate a high-resolution labelling whereas the antibodies were used at very low concentration, i.e. at a concentration of 0.03 µg/ml which is 33-fold lower than the optimal concentration of the known FSHR323 antibody. This figure also clearly demonstrates that the antibodies of the present invention: 1 to 5 allow to label FSHR at concentrations (FIG. 5 images 1 to 5) where the known FSHR323 antibody do not (FIG. 5 image 6)

In other words, this example clearly demonstrates that the antibodies of the present invention are better FSHR labelling compound and allow to detect and to obtain high resolution images. In addition, this example clearly demonstrates that the antibodies of the present invention are efficient at very low concentrations and in particular concentrations for which the known antibodies are not useful

LIST OF REFERENCES

1. Marusyk A, Almendro V, Polyak K. Nat Rev Cancer 2012; 12:323-34.
2. Keereweer S, Van Driel P B, Robinson D J, Lowik C W. Mol Imaging Biol 2014; 16:1-9.
3. Folkman J. J Clin Invest 1990; 85:433-41.
4. Siemann D W, Bibby M C, Dark G G, Dicker A P, Eskens F A, Horsman M R, Marmé D, Lorusso P M. Clin Cancer Res 2005; 11:416-20.
5. Thorpe P E. Clin Cancer Res 2004; 10:415-27.
6. Roberts W G and Palade G E. Cancer Res 1997; 57:765-72.
7. Jain R K. J Clin Oncol 2013; 31:2205-18.
8. Neri D, Bicknell R. Nat Rev Cancer 2005; 5:436-46.
9. Radu A, Pichon C, Camparo P, Antoine M, Allory Y, Couvelard A, Fromont G, Hai M T, Ghinea N. N Engl J Med 2010; 363:1621-30.
10. Renner M, Goeppert B, Siraj M A, Radu A, Penzel R, Wardelmann E, Lehner B, Ulrich A, Stenzinger A, Warth A, Vogel M N, Weichert W, Schirmacher P, Mechtersheimer G, Ghinea N. Histopathology 2013; 63:29-35.
11. Siraj A, Desestret V, Antoine M, Fromont G, Huerre M, Sanson M, Camparo P, Pichon C, Planeix F, Gonin J, Radu A, Ghinea N. BMC Cancer 2013; 13:246.
12. Planeix F, Siraj M A, Bidard F C, Robin B, Pichon C, Sastre-Garau X, Antoine M, Ghinea N. Exp Clin Cancer Res 2015; 34:12.
13. Gromoll J, Dankbar B, Gudermann T. Mol Cell Endocrinol 1994; 102:93-102.
14. Peterson V M, Castro C M, Chung J, Miller N C, Ullal A V, Castano M D, Penson R T, Lee H, Birrer M J, Weissleder R. Proc Natl Acad Sci USA 2013; 110:E4978-86.
15. Vannier B, Loosfelt H, Meduri G, Pichon C, Milgrom E. Biochemistry 1996; 35:1358-66.
16. Yang W P, Green K, Pinz-Sweeney S, Briones A T, Burton D R, Barbas C F 3rd. J Mol Biol 1995; 254:392-403.
17. Ben-Josef E, Yang S Y, Ji T H, Bidart J M, Garde S V, Chopra D P, Porter A T, Tang D G. J Urol 1999; 161:970-6.
18. Mariani S, Salvatori L, Basciani S, Arizzi M, Franco G, Petrangeli E, Spera G, Gnessi L. J Urol 2006; 175:2072-7
19. Peter J Hoskin, Radiotherapy in Practice—Radioisotope Therapy, 2007

20. Xu X, Wu J, Liu Y et al. Multifunctional envelope-type siRNA delivery nanoparticle platform for prostate cancer therapy. ACS Nano 2017; Mar. 3. doi: 10.1021/acsnano.6b07195
21. Allahyari H, Heidari S, Ghamgosha M, Saffarian P, Amani J. Immunotoxin: A new tool for cancer therapy. Tumor Biology February 2017:I-II.DOI: 10.1177/1010428317692226
22. Eisenreich A, Bolbrinker J, Leppert U. Tissue factor: A conventional or alternative target in cancer therapy. Clin Chem 2016; 62:563-70.
23. Arap W, Haedicke W, Bernasconi M, Kain R, Rajotte D, Krajewski S, Ellerby H M, Bredesen D E, Pasqualini R, Ruoslahti E. Proc Natl Acad Sci USA 2002; 99:1527-31.
24. Leuschner C, Hansel W. Biol Reprod 2005; 73:860-5.
25. Nolting B. Methods Mol Biol 2013; 1045:71-100
26. Jain N, Smith S W, Ghone S, Tomczuk B. Pharm Res 2015; 32:3526-40.
27. Tsuchikama K, An Z. Protein Cell 2016 Oct.14DOI: 10.1007/s13238-016-0323-0.
28. Rezvani K, Rouce R H. Front Immunol 2015 6:578. doi:10.3389/fimmu.2015.00578. eCollection 2015
29. Figueroa J A, Reidy A, Mirandola L, et al. Int Rev Immunol 2015; 34:154-87.
30. Tanaka E1, Choi H S, Humblet V, Ohnishi S, Laurence R G, Frangioni J V. Surgery 2008; 144:39-48.
31. WO 83/004261.
32. Köhler G, Milstein C. Nature 1975; 256:495-7.
33. Cote R J, Morrissey D M, et al. Proc Natl Acad Sci USA 1983; 80:2026-30.
34. U.S. Pat. No. 4,816,567.
35. Clackson T, Hoogenboom H R, Griffiths A D, Winter G. Nature 1991; 352:624-8 and Marks J D, Hoogenboom H R, Bonnert T P, McCafferty J, Griffiths A D, Winter G. J Mol Biol 1991; 222:581-97.

The invention claimed is:

1. An isolated antibody or antigen binding portion thereof directed against the human follicle-stimulating hormone receptor (FSHR), comprising the following:
   a variable heavy (VH) chain complementarity determining region (CDR)1 having the amino acid sequence XaXbXcXdXe (SEQ ID NO: 16) wherein Xa is Q, R or K; Xb is F, Q, S or Y, Xc is Y or W, Xd is V, L, I or T, and Xe is G, I, L, Q or T,
   a variable heavy (VH) chain complementarity determining region (CDR)-2 having the amino acid sequence EIXfPXgXhXiNTNYNEKFKG (SEQ ID NO: 11) wherein Xf is F, L or Y, Xg is R or Q, Xh T or N and Xi G or Q,
   a variable heavy (VH) chain complementarity determining region (CDR)-3 having the amino acid sequence GPTASGYAMDY (SEQ ID NO: 12),
   a variable light chain (VL) complementarity determining region (CDR)1 having the amino acid sequence RSSQSIVHRNGNTYLE (SEQ ID NO: 13),
   a variable light chain (VL) complementarity determining region (CDR)2 having the amino acid sequence KVSNRFS (SEQ ID NO: 14), or
   a variable light chain (VL) complementarity determining region (CDR)3 having the amino acid sequence FQGSHVPFT (SEQ ID NO: 15).

2. The antibody or antigen-binding portion thereof according to claim 1, wherein the variable heavy (VH) chain complementarity determining region (CDR)1 amino acid sequence is selected from the group consisting of QFYVG (SEQ ID NO: 1), RQWVI (SEQ ID NO: 2), KQWLL (SEQ ID NO: 3), RSWIL (SEQ ID NO: 4), and KYWTQ (SEQ ID NO: 5).

3. The antibody or antigen-binding portion thereof according to claim 1, wherein the variable heavy (VH) chain complementarity determining region (CDR)2 amino acid sequence is selected from the group consisting of EIFPRTGNTNYNEKFKG (SEQ ID NO: 6), EILPRNGNTNYNEKFKG (SEQ ID NO: 7), EIFPRNGNTNYNEKFKG (SEQ ID NO: 8), EIYPQNQNTNYNEKFKG (SEQ ID NO: 9), and EIYPRNGNTNYNEKFKG (SEQ ID NO 10).

4. The antibody or antigen-binding portion thereof according to claim 1, wherein the variable heavy (VH) chain complementarity determining region (CDR)1 amino acid sequence is QFYVG (SEQ ID NO: 1) and the variable heavy (VH) chain complementarity determining region (CDR)2 amino acid sequence is EIFPRTGNTNYNEKFKG (SEQ ID NO: 6).

5. The antibody or antigen-binding portion thereof according to claim 1, wherein the variable heavy (VH) chain complementarity determining region (CDR)1 amino acid sequence is RQWVI (SEQ ID NO: 2), and the variable heavy (VH) chain complementarity determining region (CDR)2 amino acid sequence is EILPRNGNTNYNEKFKG (SEQ ID NO: 7).

6. The antibody or antigen-binding portion thereof according to claim 1, wherein the variable heavy (VH) chain complementarity determining region (CDR)1 amino acid sequence is KQWLL (SEQ ID NO: 3), and the variable heavy (VH) chain complementarity determining region (CDR)2 amino acid sequence is EIFPRNGNTNYNEKFKG (SEQ ID NO: 8).

7. The antibody or antigen-binding portion thereof according to claim 1, wherein the variable heavy (VH) chain complementarity determining region (CDR)1 amino acid sequence is RSWIL (SEQ ID NO: 4) and the variable heavy (VH) chain complementarity determining region (CDR)2 amino acid sequence is EIYPQNQNTNYNEKFKG (SEQ ID NO: 9).

8. The antibody or antigen-binding portion thereof according to claim 1 wherein the variable heavy (VH) chain complementarity determining region (CDR)1 amino acid sequence is KYWTQ (SEQ ID NO: 5) and the variable heavy (VH) chain complementarity determining region (CDR)2 amino acid sequence is EIYPRNGNTNYNEKFKG (SEQ ID NO: 10).

9. The antibody or antigen-binding portion thereof according to claim 1, wherein the sequence of the heavy chain comprise a peptide selected from the group consisting of QVQLQQSGAELMKPGASVKISCKATGYTFSQFYVGWVKQRPGHGLEWIGEIFPRTGNTNYNEKFKGKATFTADTSSSTAYMQLSSLTSEDSAVYYCARGPTASGYAMDYWGQ GTSVTVSS (SEQ ID NO: 17), QVQLQQSGAELMKPGASVKISCKATGYTFSRQWVIWVKQRPGHGLEWIGEILPRNGNTNYNEKFKGKATFTADTSSSTAYMQLSSLTSEDSAVYYCARGPTASGYAMDYWG QGTSVTVSS (SEQ ID NO: 18), QVQLQQSGAELMKPGASVKISCKATGYTFSKQWLLWVKQRPGHGLEWIGEIFPRNGNTNYNEKFKGKATFTADTSSSTAYMQLSSLTSEDSAVYYCARGPTASGYAMDYWG QGTSVTVSS (SEQ ID NO: 19), QVQLQQSGAELMKPGASVKISCKATGYTFSRSWILWVKQRPGHGLEWIGEIYPQNQNTNYNEKFKGKATFTADTSSSTAYMQLSSLTSEDSAVYYCARGPTASGYAMDYWGQ GTSVTVSS (SEQ ID NO: 20), and QVQLQQSGAELMKPGASVKISCKATGYTFSKYWTQWVKQRPGHGLEWIGEIYPRNGNTNYNEKFKGKATFTADTSSSTAYMQLSSLTSEDSAVYYCARGPTASGYAMDYWG QGTSVTVSS (SEQ ID NO: 21).

10. The antibody or antigen-binding portion thereof according to claim 1, wherein the antibody is produced by Chinese Hamster Ovary (CHO) cells.

11. A pharmaceutical composition comprising the antibody or antigen-binding portion thereof of claim 1, and a pharmaceutically acceptable carrier.

12. A method of treating cancer comprising administering in an effective amount the antibody or antigen-binding portion thereof according to claim 1.

13. An in vitro method of detecting a cancerous cell in a sample, the method comprising
   contacting the sample with the antibody or antigen-binding portion thereof according to claim 1, and
   detecting binding of the antibody or antigen-binding portin thereof with FSHR or a fragment thereof in the sample, wherein binding indicates the presence of the cancerous cell.

14. An in vitro imaging method, optionally a cancer image method, comprising
   contacting a sample with the antibody or antigen-binding portion thereof according to claim 1,
   detecting binding of the antibody or antigen-binding portion thereof with FSHR or a fragment thereof in the sample, wherein binding indicates the presence of FSHR or a fragment thereof in the sample.

15. An in vivo imaging method, optionally a cancer imaging method, comprising
   administering to a human or an animal an imaging effective amount of the antibody or antigen-binding portion thereof according to claim 1; and
   detecting binding of the antibody or antigen-binding portion thereof with FSHR or a fragment thereof in the human or animal, wherein binding indicates the presence of FSHR or a fragment thereof in the sample.

* * * * *